US012377178B2

(12) United States Patent
Mullen et al.

(10) Patent No.: US 12,377,178 B2
(45) Date of Patent: Aug. 5, 2025

(54) UV-C VIRUS INACTIVATION DEVICES AND SUPPRESSING SOUND AND OPERATING THE SAME

(71) Applicant: Dynamics Inc., Cheswick, PA (US)

(72) Inventors: Jeffrey D. Mullen, Glenshaw, PA (US); Andrew Veter, Pittsburgh, PA (US); Keith Huthmacher, Pittsburgh, PA (US); Peter Gilgunn, Pittsburgh, PA (US); James Nelson, Rillton, PA (US); David Malarik, Worthington, PA (US); Jun Yu, Pittsburgh, PA (US)

(73) Assignee: Dynamics Inc., Cheswick, PA (US)

( * ) Notice: Subject to any disclaimer, the term of this patent is extended or adjusted under 35 U.S.C. 154(b) by 579 days.

(21) Appl. No.: 17/215,402

(22) Filed: Mar. 29, 2021

(65) Prior Publication Data
US 2021/0299303 A1    Sep. 30, 2021

Related U.S. Application Data

(60) Provisional application No. 63/140,237, filed on Jan. 21, 2021, provisional application No. 63/109,333,
(Continued)

(51) Int. Cl.
*A61L 2/10* (2006.01)
*A61K 39/12* (2006.01)
(Continued)

(52) U.S. Cl.
CPC .............. *A61L 2/10* (2013.01); *A61K 39/12* (2013.01); *A61L 2/0047* (2013.01);
(Continued)

(58) Field of Classification Search
CPC ........ A61L 2/10; A61L 2/0047; A61L 2/0052; A61L 2/24; A61L 2/26; A61L 9/20;
(Continued)

(56) References Cited

U.S. PATENT DOCUMENTS 8,337,770 B2 * 12/2012 Wind ................... A61L 2/10
  250/455.11
2007/0187626 A1 * 8/2007 Gaska ................... A61L 2/10
  250/504 R
(Continued)

FOREIGN PATENT DOCUMENTS

CN      206120779 U   *  4/2017
WO      WO-0195964 A1 * 12/2001 ............ A61M 16/00

*Primary Examiner* — Michael Maskell
(74) *Attorney, Agent, or Firm* — Morris Law Group; Robert W. Morris

(57) ABSTRACT

An UV-C device may include several UV-C light sources (e.g., UV-C LEDs) and such UV-C LEDs may have UV-C reflecting structures arranged to direct UV-C in a particular direction and at a particular size and shape. Doing so may, for example, increase the UV-C in a particular direction or working area. A UV-C generating device may be utilized in an air stream, such as an air duct, to sterilize air from that air stream. Sound suppression compartments may be placed around a UV-C generating device inlet and/or a device outlet to reduce sound from the UV-C generating device. Human perceivable (e.g., audible, tactile, and/or visual) notifications may be utilized to provide notification of different modes of operation and/or different efficacy levels (e.g., percent ranges of inactivation of a particular or multiple particular viruses, bacteria, spores, etc.

11 Claims, 12 Drawing Sheets

Related U.S. Application Data filed on Nov. 3, 2020, provisional application No. 63/085,134, filed on Sep. 29, 2020, provisional application No. 63/085,140, filed on Sep. 29, 2020, provisional application No. 63/056,534, filed on Jul. 24, 2020, provisional application No. 63/042,494, filed on Jun. 22, 2020, provisional application No. 63/023,845, filed on May 12, 2020, provisional application No. 63/018,699, filed on May 1, 2020, provisional application No. 63/015,469, filed on Apr. 24, 2020, provisional application No. 63/009,301, filed on Apr. 13, 2020, provisional application No. 63/006,710, filed on Apr. 7, 2020.

(51) Int. Cl.

| | |
|---|---|
| *A61L 2/00* | (2006.01) |
| *A61L 2/24* | (2006.01) |
| *A61L 2/26* | (2006.01) |
| *A61L 9/20* | (2006.01) |
| *A61M 16/04* | (2006.01) |
| *A61M 16/06* | (2006.01) |
| *B01D 53/00* | (2006.01) |
| *C02F 1/32* | (2023.01) |
| *F24F 8/22* | (2021.01) |
| *F24F 13/20* | (2006.01) |
| *H05K 1/03* | (2006.01) |
| *A61K 39/00* | (2006.01) |
| *G06F 3/0482* | (2013.01) |
| *G06F 3/04847* | (2022.01) |

(52) U.S. Cl.
CPC ............ *A61L 2/0052* (2013.01); *A61L 2/24* (2013.01); *A61L 2/26* (2013.01); *A61L 9/20* (2013.01); *A61M 16/047* (2013.01); *A61M 16/0666* (2013.01); *B01D 53/007* (2013.01); *C02F 1/325* (2013.01); *F24F 8/22* (2021.01); *F24F 13/20* (2013.01); *H05K 1/038* (2013.01); *A61K 2039/5252* (2013.01); *A61L 2202/11* (2013.01); *A61L 2202/122* (2013.01); *A61L 2202/14* (2013.01); *A61L 2202/15* (2013.01); *A61L 2202/16* (2013.01); *A61L 2202/21* (2013.01); *A61L 2202/24* (2013.01); *A61L 2209/111* (2013.01); *A61L 2209/12* (2013.01); *A61L 2209/134* (2013.01); *A61L 2209/16* (2013.01); *B01D 2259/804* (2013.01); *C02F 2201/3222* (2013.01); *C02F 2201/3227* (2013.01); *C02F 2201/326* (2013.01); *F24F 2013/205* (2013.01); *G06F 3/0482* (2013.01); *G06F 3/04847* (2013.01); *H05K 2201/05* (2013.01)

(58) Field of Classification Search
CPC ........... A61L 2202/11; A61L 2202/122; A61L 2202/14; A61L 2202/15; A61L 2202/16; A61L 2202/21; A61L 2202/24; A61L 2209/111; A61L 2209/12; A61L 2209/134; A61L 2209/16; A61L 2202/25; A61K 39/12; A61K 2039/5252; A61M 16/047; A61M 16/0666; A61M 16/00; B01D 53/007; B01D 2259/804; C02F 1/325; C02F 2201/3222; C02F 2201/3227; C02F 2201/326; F24F 8/22; F24F 13/20; F24F 2013/205; H05K 1/038; H05K 2201/05; G06F 3/0482; G06F 3/04847; Y02A 50/20
USPC ........................ 250/455.11, 504 R
See application file for complete search history.

(56) References Cited

U.S. PATENT DOCUMENTS

| | | | |
|---|---|---|---|
| 2015/0297768 A1* | 10/2015 | Bettles | ...................... A61L 2/10 250/455.11 |
| 2018/0050123 A9* | 2/2018 | Krosney | .............. B01D 53/007 |

* cited by examiner

UV-C VIRUS INACTIVATION DEVICES AND SUPPRESSING SOUND AND OPERATING THE SAME

CROSS-REFERENCE TO RELATED APPLICATION

This application claims the benefit of U.S. Provisional Patent Application Nos. 63/140,237, titled "LARGE-SCALE UV-C INACTIVATION DEVICES AND SIMULATIONS OF THE SAME," filed Jan. 21, 2021, 63/109,333, titled "INCREASING EFFICIENCY OF UV-C INACTIVATION DEVICES," filed Nov. 3, 2020, 63/085,140, titled "UV-C VIRUS INACTIVATION DEVICES AND SUPPRESSING SOUND AND OPERATING THE SAME," filed Sep. 29, 2020, 63/085,134, titled "UV-C VIRUS INACTIVATION DEVICES AND SUPPRESSING SOUND AND OPERATING THE SAME," filed Sep. 29, 2020, 63/056,534, titled "SYSTEMS AND METHODS FOR UV-C INACTIVATED VIRUS VACCINES AND UV-C SANITIZATION," filed Jul. 24, 2020, 63/042,494, titled "SYSTEMS AND METHODS FOR EFFICIENT AIR STERILIZATION WITHOUT CIRCULATION UNSANITIZED AIR," filed Jun. 22, 2020, 63/023,845, titled "SYSTEMS AND METHODS FOR HANDS-FREE OBJECT STERILIZATION," filed May 12, 2020, 63/018,699, titled "SYSTEMS AND METHODS FOR UV-C SURFACE STERILIZATION," filed May 1, 2020, 63/015,469, titled "SYSTEMS AND METHODS FOR INCREASING WORK AREA AND PERFORMANCE OF UV-C GENERATORS," filed Apr. 24, 2020, 63/009,301, titled "UV-C AMPLIFIERS AND CONTROL OF THE SAME," filed Apr. 13, 2020, 63/006,710, titled "SYSTEMS, DEVICES AND METHODS FOR ULTRA-DENSE, FLEXIBLE LED MICRO-ARRAYS FOR IN VIVO VIRAL LOAD REDUCTION," filed Apr. 7, 2020, 63/003,882, titled "SYSTEMS, DEVICES AND METHODS FOR ULTRA-DENSE, FLEXIBLE LED MICRO-ARRAYS FOR IN VIVO VIRAL LOAD REDUCTION," filed Apr. 1, 2020, 63/001,461, titled "SYSTEMS, DEVICES AND METHODS FOR ULTRA-DENSE, FLEXIBLE LED MICRO-ARRAYS FOR IN VIVO VIRAL LOAD REDUCTION," filed Mar. 29, 2020, each of which is hereby incorporated by reference herein in its entirety.

BACKGROUND OF THE INVENTION

This invention relates to sterilization.

SUMMARY OF THE INVENTION

A UV-C generation device is provided that includes multiple UV-C light emitting diodes ("LEDs") positioned around a work area. For example, the multiple UV-C LEDs may be positioned around a cylinder. The cylinder may be, for example, comprised of a UV-C transparent material (e.g., a material with UV-C transparency greater than fifty percent (50%) such as, for example, quartz or UV-C transparent polymer. The LEDs may be located on a flexible printed circuit board. The flexible printed circuit board may be fabricated, for example, from a polyimide or FR4 and may be, for example between 2 thousandths of an inch and seven thousandths of an inch thick (e.g., between 2 and 4 thousandths of an inch thick such as between 2 and 2.5 thousandths of an inch thick). A working substance (e.g., a gas, a liquid, an air and liquid, a virus solution for inactivation for vaccine creation) may flow through the cylinder and the UV-C LEDs may interact with the working substance to, for example, sterilize the working substance. The UV-C LEDs may, for example, have a wavelength between 200 and 280 nanometers (e.g., between 220 and 280 nanometers or between 250 and 265 nanometers or between 255 and 260 nanometers such as 255, 260, or 265 nanometers).

Each UV-C LED may be independently controlled and regulated through control and regulation circuitry on the flexible printed circuit board or another device. Accordingly, the intensity of each UV-C LED as well as the turn-ON time and turn-OF time of each UV-C LED may be independently controlled. A processor may be provided on the flexible circuit board or on another communicatively coupled device to control the operation of the UV-C LEDs.

The flexible printed circuit board may be, for example, wrapped around all of, or a portion of, the cylinder so that the UV-C LEDs may provide UV-C light into the cylinder through the cylinder wall. UVC-LEDs may be arranged in rows and columns. A UV-C flexible circuit when wrapped around a cylinder may, for example, have rows of three (3) UV-C LEDs in multiple columns (e.g., three columns, six columns, nine columns, twelve columns, more than twelve columns, or any number of columns). Accordingly, six columns of three UV-C LEDs would provide eighteen UV-C LEDs. The UV-C LEDs may be aligned in rows or staggered in rows around the cylinder. Persons skilled in the art will appreciate that the workspace may not be provide din a cylinder but in any shape that provides a workspace (e.g., inside a cube, rectangular, triangular, or any other type of housing).

UV-C reflective material may be provided on the flexible printed circuit board around the UVC-LEDs or selectively provided, around the UV-C LEDs placement so as to not generally impede UV-C emanating from the UV-C LEDs, on the interior surface or exterior surface of the cylindrical housing. Such a UV-C reflective material may include, for example, aluminum.

One or more heat sinks may be provided around the UV-C LEDs in order to capture and expel heat from UV-C LEDs away from those UV-C LEDs. A battery and/or wall plug and/or battery and wall-plug may be utilized to charge, for example, one or more rechargeable batteries located inside a housing that includes the working space.

Manual inputs may be operable to receive manual input from outside of a housing that may include the working area (e.g., a UV-C transparent cylinder) or be placed within the proximity of a working area. Temperature, humidity, and flow rate may be added and utilized to, for example, control the intensity of one or more of the UV-C LEDs so that, for example, the intensity may be changed for different temperatures, flows, and/or humidity.

Persons skilled in the art will appreciate that other types of Ultraviolet LEDs, or other light sources, may be provided on an LED array such as UV-B and UV-A LEDs. Similarly, additional wavelengths of light may be provided in LEDs, or other types of light sources. A spectrometer, or other device, may be included to determine the type of material in the working space and may activate different LEDs or different types of LEDs (e.g., based on the detected material(s)). Similarly, different UV-C LEDs, or non-LED UV-C sources, may provide different wavelengths and different modes may be provided to control the UV-C LEDs so a subset of the UV-C LEDs may provide a particular nanometer wavelength (e.g., 255 to 265 nanometers) and other UV-C LEDs may provide another particular nanometer wavelength (e.g., 270 to 280 nanometers).

A flexible circuit board does not have to be rolled, for example, for the flexible circuit board to sterilize a working surface. A device may have a generally flat flexible circuit board at a perimeter separated from a surface that has contaminant (e.g., virus and/or bacteria) that requires sterilization). The housing may have a handle (e.g., a removable handle) so that the UV-C sterilization device can be provided as want for moving over, and sterilizing, a surface.

The housing may include multiple mateable ports for handles such that, for example, one handle may be inserted into one mateable port to provide a sanitizing and a larger handle may be inserted into a different mateable port to provide a sanitizing mop/broom. Such a UV-C sanitizing device may be wall mounted such that, for example, someone can place their hands in a working space and have their hands sterilized. The device may operate on two modes—human mode and non-human mode. The device can prompt this to the user for the mode, wait for the user to activate the mode, or autonomously activate the mode.

The flexible circuit board with multiple UV-C LEDs may be articulated via motors and/or other controls so that different areas that, for example, include UV-C LEDs may be moved away from each other or to each other or moved closer to, or further away from, the other LED's.

Persons skilled in the art will appreciated that a fixed distance surface cleaner may be utilized. A fixed distance surface cleaner may be, for example, permanently attached (e.g., bolted and/or screwed) to a surface (e.g., a counter-top) so that objects may be passed in front of UV-C generating portion(s) to sterilize the objects. For example, a UV-C surface sanitizer may be provided on a countertop next to a point-of-sale register. A customer may pass a credit card and or a currency bill and/or a coil under a UV-C sanitization device to sanitize a device. A UV-C generating device may be embedded in the countertop or placed in the countertop and may face upwards so an object provided over it may be sanitized on the surface(s) facing the UV-C generation. UV-C generation units may provide a particular amount of UV-C light at a particular point and may be controlled, over time, to provide that amount of UV-C light at that particular point. Accordingly, for example, UV-C light may be provided at an amount that sterilizes at a particular distance (e.g., under 5 millimeters from the surface of a counter) but not at a further point (e.g., beyond 5 millimeters) from the surface of a counter. UV-C generators may be provided over and/or under a conveyer (e.g., a gapped and/or conveyer with UV-C transparent material).

A UV-C air sterilization device is provided in which a fan (e.g., axial fan and/or centrifugal fan) pushes and/or pulls air through a working area into which UV-C is applied. The air may then be directed over the UV-C sources of light so that the sterilized air is also used to remove heat from the UV-C sources. The circulated air that has been sanitized and utilized to remove heat from the sanitization device may then be, for example, expelled from the device. In doing so, the device may move sanitized air from the device without moving non-sanitized air from the device.

An air sanitization device may also apply other types of light such as UV-A and/or UV-B light in addition to, or in place of, UV-C light. A fan may have several speeds such that different efficacies of sterilization may be provided and/or different air speeds may be provided.

One or more fixed and/or removable mechanical particulate filters may be provided (e.g., before the working area of the UV-C sanitization device). In doing so, particulates may be kept away from A UV-C working area of the device.

One or more (e.g., several) speed settings may be provided to circulate air through a UV-C working area. Such various speeds may, for example, provide different impact rates (e.g., inactivation rates) of various air-born contaminants (e.g., virus) and may provide different speeds at sanitizing air.

An autonomous cleaning operation may be provided by a UV-C sanitization device that may clean a UV-C generating device. For example, an air sterilization device may utilize one or more fans to move air through a UV-C working area at a maximum speed during operation. However, during cleaning, the one or more fans may move the air through the UV-C working area at a faster rate and such a faster rate may be constant for a period of time or may include several pulses of air. A cleaning substance may also be released to be moved through the working area during an autonomous leaning operation. A portion of a UV-C air sterilization device may be accessible to a user so that the user may, for example, access a UV-C working area of a UV-C air sanitization device for cleaning. Cleaning objects (e.g., a brush that can fit into the working area of a UV-C sanitization device, cloth, and/or other object may be provided in a sealed box with the UV-C air sanitization device for consumer sale). A UV-C sanitization device may have an indicator (e.g., verbal and/or audible) to provide a notification to a user that a user-driven and/or user-assisted cleaning process is desired. A housing of a UV-C sanitization device may include, for example, a mating structure such that a cleaning object may be mated to the UV-C sanitization device.

One or more light sources (e.g., visible light sources) may be placed in one or more working areas of a UV (e.g., UV-A, UV-B, and/or UV-C) air sanitization device and one or more sensors that can detect the light provided from those light sources may be placed in the working channel or areas where light from the light sources may reach. Persons skilled in the art will appreciate that different intensities of light sensed may, for example, be indicative of different amounts of residue (e.g., dirt and/or dust) that may have gathered on the surfaces of a UV-C working area as different amounts of residue may decrease, for example, the reflectivity of the surfaces with the reside. Persons skilled in the art will appreciate that materials that are transparent to particular wavelengths may be utilized in a uV-C working area. Light (e.g., visible and/or non-visible light) may be provided through these transparent materials and sensors may be utilized to determine any residue on such transparent materials. Accordingly, light sources (e.g., visible light and/or non-visible light sources) may be utilized with sensors to determine the state of cleanliness of UV-C working surfaces by detecting different amounts of residue. Additionally, for example, UV-C sensors may be utilized to determine the amount of UV-C light in particular areas to determine, for example, how much reflectivity and/or transparency has been degraded from residue over reflective and/or transparent materials in and/or around a UV-C working area, respectively. Residue may be, for example, determined by direct sensing means such as for example a camera that takes a picture and analyzes the picture.

A reflective perimeter may be placed around a UV-C light source such that, for example, UV-C light is directed in a particular direction. Additionally, for example, UV-C reflective materials may be utilized to improve UV-C mating between a UV-C LED and a UV-C transport medium (e.g., a UV-C fiber optic).

UV-C may be utilized to inactivate amounts of a virus (e.g., SARS-CoV-2) in a substance, such as the air, order to create a vaccination such as a aerosolized vaccination. Inactivated virus may then be breathed in to have a vaccination impact. Such an aerosolized vaccination, or another form (e.g., liquid) vaccination may be provided by an inactivation fan that inactivates air or in a ventilator, or other medical device, as an air inactivation device. In an example of ventilator, or other device, fans may not be provided to move air through an inactivation working area as the ventilator, or other device, may utilize move air, or another substance (e.g., liquid), through the inactivation working area. UV inactivation of virus to create vaccines may be performed, for example, with UV-C. Multiple strains of virus (e.g., strains from different claves of virus) may be inactivated and combined in order to form a super vaccination across one, two, or more than two virus, strains of virus from the same clave, strains of virus strains of a virus from different claves. For example, a multi-strain vaccination may include strains of a virus from at least 3 or at least 5 different claves. Accordingly, for example, a multi-clave vaccination may be provided by inactivating with UV-C one or more virus strains from multiple or several claves of SARS-CoV-2 and combining the inactivates virus strains in a single vaccine for administration to a human being. Persons skilled in the art will appreciate that the amount of different strains of a virus may be the same. A vaccination may have any number of inactivated virus such as, for example, one million, ten million one hundred million, one billion, or more than one billion virus and may have one inactivated strain, more than one inactivated strain, and the inactivated strains may be provided in equal proportions or different proportions.

One or more UV-C air sterilization devices may be, for example, placed in an air duct (e.g., 24 inch by 24 inch, 36 inch by 36 inch, 48 inch by 48 inch, circular air duct, and/or rectangular air duct). One or more UV-C air sanitization devices may be placed after an air register bringing air into an air duct and/or room or before an air register bringing out of an air duct and/or room. Such devices may be provide on a structure that forces all, or most, of the air to go through the UV-C air sanitization devices. Each air sanitization device may have, for example, one or more fans (e.g., two fans where each fan includes two counter-rotating blades). The structure may be expandable and collapsible so that the air sanitization device may be utilized in different size and/or shape air ducts. One or more controllers may be on the structure and/or one or more of the UV-C air sanitization devices that may control all of the devices (e.g., control which fans are ON/OFF and the speeds of each fans) and may receive information from the devices (e.g., if a device needs servicing such as UV-C LEDs need to be replaced to maintain a particular efficacy). Persons skilled in the art will appreciate that one or more redundant air sanitization devices may be included such that one or more of the air sanitization devices loose efficacy (e.g., UV-C LEDs fall below a performance threshold so the UV-C air sanitization devices falls below a performance threshold) redundant UV-C air sanitization devices may be turned ON. Alternatively, for example, all UV-C sterilization devices may be ON and the speed of fans (if included in an air sanitization device) may be adjusted based on the number of UV-C air sanitization devices in an array and the current operating efficacy of the array. Sensors may be utilized in the UV-C generating devices to determine the amount of UV-C being generated (e.g., by detecting UV-C light or another light emitted such as visible light, UV-B light, and/or UV-A light).

Persons skilled in the art will appreciate that air registers for a building may deliver within a particular range (e.g., 200 to 500 CFM). Accordingly, for example, an array of 3 fans at that can deliver at least 70 CFM of sanitized air may be placed in an array and utilized to sterilize the air produced by an air register providing air at 200 CFM. Three air sanitization devices producing sanitized air at a particular efficacy (e.g., 99% or greater) at a speed of at least 100 CFM may be utilized and if one of the air sanitization devices needs to be taken off-lien or the efficacy falls, the other two devices may continue to sanitize air at the desired efficacy. An array of four UV-C devices may be utilized, for example, that may be able to sanitize air utilizing UV-C at an efficacy of at least 70 CFM such that if one UV-C sanitization device is not operating, the three other UV-C sanitization devices may provide UV-C sanitization of at least 210 CFM.

Persons skilled in the art will appreciate that UV-C generating devices may operate at different efficacies over time under different types of operating regimes as, for example, intensity of UV-C light sources decay (e.g., intensity of UV-C light emitting diodes degrade). For example, UV-C LEDs may be operated at high current and may decay faster in some instances than if those UV-C LEDs were operated at a lower current. As per another example, UV-C LEDs at a particular current may degrade different based on, for example, how an LED is pulsed. For example, a UV-C LED that is pulsed so it is ON more in a particular amount of time than a pulse regime where it is ON less in that particular amount of time may degrade faster. Program logic, such as program logic stored in a memory and run by a processing circuit (e.g., a processor) may, for example, estimate the intensity of UV-C light for one or more UV-C light sources (e.g., UV-C LEDs) over time. As modes are changed (e.g., intensity is turned down autonomously or manually), the estimation may be updated using stored information indicative of decay curves associated with those various modes or through other estimation processes (e.g., utilizing light sensors to determine the amount of light being produced by one or more light sources). One or more notification structures (e.g., visible spectrum LEDs, displays, speakers, and/or tactile generators) may provide human perceivable notifications periodically, upon request (e.g., manual request), or at particular events (e.g., each time a device is turned ON or a mode is changed). For example, three visible spectrum LEDs may be provided. Each visible spectrum LED may be associated with a different operational mode. Each operational mode may be associated with a different fan speed. Accordingly, for example, a consumer may select (e.g., via a mobile application on a mobile phone, a website on a device such as a laptop, or using an interface such as a toggle button on the device) a fan speed and a light corresponding to that van speed may provide an indication the associated mode has been selected. Accordingly, a fan may have, for example, a "low" airspeed, a "medium" airspeed, and a "high" airspeed. Airspeeds for a device may be, for example, 100 liters per minute ("LPM"), 200 LPM, and 400 LPM. For example, airspeeds may be different by at least 100 LPM (e.g., 100 LPM, 200 LPM, and 300 LPM). Alternatively, for example, airspeeds may be different by at least 500 LPM (e.g., 500 LPM, 1,000 LPM, and 1,500 LPM). One or more manual interfaces (e.g., one or more buttons or touch interfaces) may be provided (e.g., a touch-sensitive display may be provided). Such manual interfaces may select any number of modes (e.g., any number of fan speeds). A digital number may be provided associated with a fan speed on a display, for example, and an manual interface (which may be the display itself) may be utilized to increase and/or decrease the fan speed by the manually controllable increments of the device (e.g., 1 LPM or 1 cubic feet per minute CFM). A consumer may change between different metric systems (e.g., LPM or CFM) on a display in order to personalize the device to a desired metric system. Similarly, for example, a language (e.g., English, Japanese, etc.) may be selected and the system may provide notifications and other display screens in the desired language.

Persons skilled in the art will appreciate that devices may monitor the intensity, and other attributes, of light sources (e.g., UV-C LEDs) and utilize this information to estimate inactivation rates at a particular period of time/operation for a particular pathogen (e.g., a particular virus, spore, bacteria, etc.) and/or estimate inactivation rates based on any attribute (e.g., the time the device is ON in a particular mode). Accordingly, for example, a device may provide notifications for different inactivation thresholds. For example, a device may have an inactivation range of 90-99% for a virus (e.g., SARS-CoV-2) during a first efficacy period, an inactivation range of 75%-89.9 percent during a second efficacy period, an inactivation range of 50% to 74.9$ during a third efficacy period, and an inactivation range of 1 to 49.9% during a fourth efficacy period. Different modes (e.g., different speeds such as 100 LPM, 200 LPM, and 400 LPM) may have different times under different efficacy periods as the different modes may utilize different intensities of lights to achieve those efficacy periods (e.g., as slower moving air may utilize less UV-C light to inactivate at a particular efficacy and, as a result, utilize less energy and provide less degradation in the light source). Light sources may be operated in different wants for different modes and/or during different efficacy ranges. For example, one or more light-emitting diodes may be turned ON (e.g., pulsed at a particular rate) and the diodes may degrade over time and the efficacy of the one or more light-emitting diodes may decrease with time. As per another example, a current may be selected at a point in the efficacy range and as the light emitting diode degrades the current may be increased so that the degradation is countered. Doing so, for example, may extend the amount of time a device can provide efficacy at a particular efficacy level. Multiple operation regimens for one or more LEDs may be provided in an efficacy range. For example, one or more UV-C LEDs in a range of efficacy of 1% to 49.9% may first operate to sustain efficacy at 25% (e.g., by providing a current to provide 25% and then increasing current as the UV-C degrades) and then sustaining efficacy at 15% and then, after that is complete, running the UV-C LEDs to a lower amount (e.g., 1%). At the end of an efficacy range, the device may provide a fault code to the consumer (e.g., by flashing one or more visible spectrum LEDs in a sequence such as a countdown sequence and then showing a fault code) so the consumer is made aware that one or more UV-C LEDs should be changed (e.g., either via a consumer or via a third party). A communications antenna may be provided in the device and the device may communicate directly to a third-party light source provider or to a device of the user (e.g., a mobile phone) to notify the consumer of the need for a light-source change. A consumer may control any aspect of a UV-C inactivation device on any other device via wired or wireless communications between that device and the UV-C inactivation device (e.g., through one or more intermediary devices). Whenever a device is turned ON, changed to a new mode, or any other event, a user notification may be provided to indicate the efficacy mode of the device at that particular period of time. For example, two, three, or more than three LEDs may be utilized for different fan speeds. When a fan speed is entered a visible spectrum LED associated with that fan speed may not blink if it is in a first efficacy level, may blink twice if it is in a second efficacy level (e.g., and then the LED may stay ON), may be three times if it is in a third efficacy level, may blink four times if it is in a fourth efficacy level, and so on for any number of efficacy levels. Notifications may be sent to various devices (e.g., mobile phones associated with one or more users) as a result of the change in efficacy level (e.g., for a particular mode such as a particular fan speed). Persons skilled in the art will appreciate that a device, for example, may have a mode of operation, for example, having at least four efficacy range levels and may have at least, for example, 750 hours of operation in each of those efficacy range levels (e.g., at humidity greater than 50%). An efficacy range level may have over, for example, at least 1,000 hours of operation or, for example, at least 2,000 hours of operation.

Persons skilled in the art will appreciate that a device may be controlled not by fan speed but, for example, an efficacy (e.g., or both). For example, a user may select different efficacy ranges and the device may, if the efficacy ranges are available, drive the UV-C light sources to provide the desired efficacy. If the efficacy is no longer available, the user may receive a notification that the efficacy is no longer available (e.g., via visual indications such as visible LED indications and/or display indications). A device may include interfaces (e.g., a touch screen display) to provide controls of the device for any type of operation such as, for example, to provide a time extension operation (e.g., sustain light sources at a particular point, such as a lower point, of an efficacy level) or to maximize efficacy for a particular time (e.g., provide the most or a relatively higher current point through a light source for a particular time). In doing so, the lifetime of a device may be extended and the inactivation rate of a device may be increased depending on a particular application and/or situation for a particular period of time or environment. Persons skilled in the art will appreciate that a humidity sensor may be provided and readings from such a humidity sensor may be utilized to impact efficacy ranges at a particular time or utilized to conserve power (e.g., lowering current during parts of relatively lower humidity compared to a higher current during parts of relatively higher humidity).

Sound suppression structures and chambers may be added to a device in order to reduce the sound that can reach a user. Such sound suppressors may be utilized to reduce sound around a particular part or in a particular direction of a device. For example, a sound suppressor chamber may be provided before the inlet to air fans pulling air into a working area by providing a mechanical sound barrier (e.g., plastic and/or metal) in line with the fans at the inlet and having air move into a chamber and around the sound barrier so that sound is contained in the chamber. The chamber may be filled with soundproofing material (e.g., soundproofing foam) and may be more than two inches in length at its largest length point, two inches in width at its largest width point, and more than two inches deep at its largest depth point (e.g., more than two inches in height such as three inches in height or more than 3 inches in height). Soundproofing coatings may be provided on any surface. Furthermore fans may be isolated in harnesses or via a mechanical absorbing structure such as a rubber so that vibrations in the fans are reduced in travel to other structures of the inactivation device.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which.

DETAILED DESCRIPTION OF THE INVENTION

Figure 1:
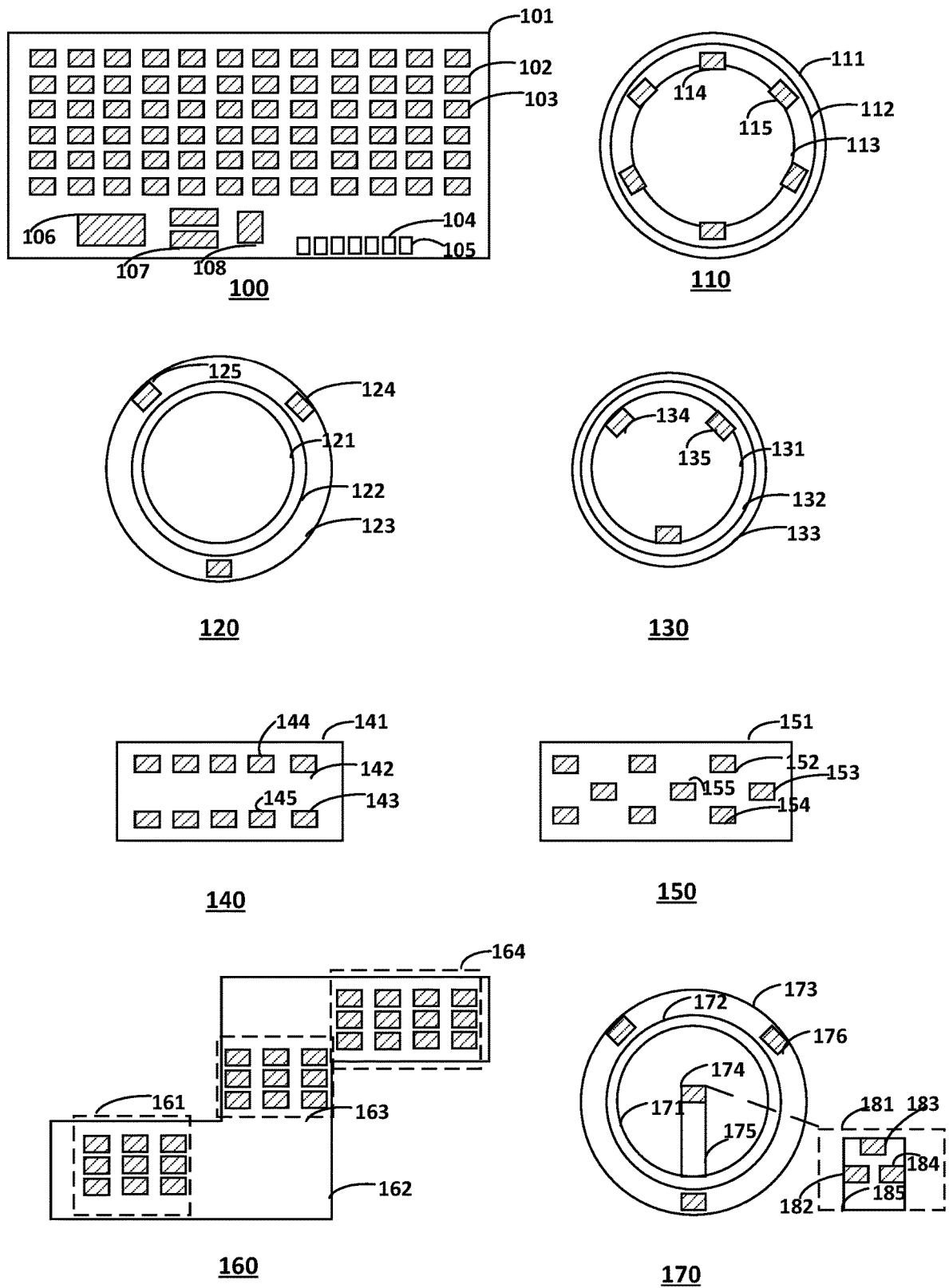
FIG. 1 are illustrations of UV-C devices constructed in accordance with the principles of the present invention.

FIG. 1 shows device 100 that may include any number of ultraviolet C (UV-C) light sources such as UV-C light emitting diodes 102 and 103. UV-C sources may have a wavelength between approximately 200 nanometers and 280 nanometers. Processor 106 and additional circuitry 107 may be included on circuit board 101 in additional to input/output ports 104 and 105.

Printed circuit board 101 may be, for example, a non-flexible or a flexible printed circuit board. Input/output ports 104 and 105 may be, for example, contacts to couple to another circuit board or an external device. Processor 106 may, for example, control UV-C LEDs 102 and 103 using firmware that is downloaded into processor 106 or provided in a memory of processor 106 before or after placement on circuit board 101. Persons skilled in the art will appreciate that printed circuit board 101 may be multiple printed circuit boards that are communicatively coupled together to form a multiple circuit board device. Different circuit boards of a multiple circuit board device may be provided in a single housing or in different housings.

Firmware updates may be downloaded through input/output ports 104 and 105. Any number of input/output ports may be provided and different protocols may be utilized for different ports. Additionally, blue-tooth (e.g., BLE), contact-less (e.g., RFID), telecommunications (e.g., cellular such as 4G or 5G cellular), infrared, or other wireless communication structures may be provided such as wireless communication chips, circuitry, protocols, and ports may be provided. Wireless power generation may be provided and may be utilized by power circuitry to change a battery coupled to printed circuit board 101 (e.g., through battery contact pads on circuit board 101).

Printed circuit board 101 may be a flexible polyimide or flexible Fr$. Persons skilled in the art will appreciate that such a flexible printed circuit board may be, for example between two thousandths of an inch and seven (7) thousands of an inch in thickness (e.g., between two thousandths of an inch and three thousands of an inch in thickness). Silicon chips may be grinded and polished before placement on printed circuit board 101 to between, for example, five thousandths and ten thousandths of an inch in thickness). Such chips may be mounted on printed circuit board 1010 via a flip-on-flex structure or via a wire-bonded structure. A wire-bonded structure may be for example a low-provide wire-bonded structure with wire-bonds that are placed with less than a five thousandths of an inch profile above the silicon chip and encapsulant that is less than three thousandths of an inch above each wire-bond The entire thickness from the bottom of flexible circuit board to the top of an encapsulant of a chip may be, for example under fourteen thousandths of an inch thick (e.g., under twelve thousandths of an inch thick). For example, the thickness from the bottom of circuit board 101 to the top of the encapsulant may be between ten and sixteen thousandths of an inch thick (e.g., between twelve and fourteen thousandths of an inch thick). Wire-bonds may be for example, gold wire-bonds or aluminum wire-bonds. A low-profile encapsulant may be provided that utilizes at least two separate encapsulate provisioning steps in order to provide the low-profile encapsulant.

Processor 106 may be one or more processors and may be provided between, for example, twenty megahertz and five gigahertz. Persons skilled in the art will appreciate that faster processors may provide faster control of UV-C LEDs 102 and 103. Faster control of UV-C LEDs may provided shorter ON times which may provide the ability to damage and sterilize certain elements (e.g., virus) without damaging and sterilizing other elements (e.g., living tissue and cells). Processor 106 may, for example, provide ON times for UV-C LEDs 102 and 103 less than, for example, 100 nanoseconds, less than 10 nanoseconds, less than 1 nanosecond. For example, Processor 106 may turn ON UV-C LEDs 102 and 103 between approximately 1 and 100 nanoseconds (e.g., between 20 and 60 nanoseconds or between 30 and 50 nanoseconds). High speed control circuitry may also be provided in order to control UV-C LEDS 102 and 103 between 1 and 100 femtosecond (e.g., between 1 and 50 femtoseconds or between 1 and 20 femtoseconds).

Circuitry 107 and 108 may include, for example, regulation and control circuitry for UV-C, or other, sources of light on circuit board 101 as well as sources of light and other circuitry on other boards or external devices. Persons skilled in the art will appreciate that UV-C LEDs on circuit board 101 may be, fore example, individually regulated and controlled or controlled as a group or in subsets. For example, circuit board 101 may include over ten (10) or over one hundred (100) UV-C LEDs. UV-C LEDs may be regulated and controlled in groups of two or more (e.g., three or more). A portion of UV-C LEDs may be regulated and controlled independently while another portion of UV-C LEDs may be regulated as a group or in sub-groups.

UV-C LEDs on printed circuit board 101 may be, for example, UV-C LEDs having the same wavelength of may have different wavelengths and they may be independently controlled at different times using different control profiles that provide different turn ON an turn OFF pulses (e.g., the duration of an OFF state for one or more UV-C LEDs may be the same duration or a different duration such as a longer or shorter duration than the ON duration for the respective one or more UV-C LEDs). The UV-C LEDs may all be between approximately 200 and 280 nanometers (e.g., provided at or between 250 and 270 nanometers such as provided at or between 255 and 265 nanometers). Some UV-C LEDs may be provided, for example, at or between 250 and 260 nanometers while others are provided, for example, at or between 260 and 270 nanometers. One or more additional light sources may be provided on board 101 such as, for example, UV-B, UV-A, VUV, and visible spectrum light sources.

Visible spectrum light sources may be provided, for example, to provide a visual indicator when board 101 is ON or OFF as well as different operating modes. For example, a visible spectrum LED may be a single-color LED (e.g., white, green, blue, Or red) or a multiple color LED and may provide indication of when a battery (e.g., a rechargeable battery) is low and/or critically low on power. Manual inputs may be included on circuit board 101 to receive, for example, manual input to turn circuit board 101 ON, Off, and/or change between different modes of operation (e.g., different intensities for UV-C LEDs 102 and 103).

Circuit board 101 may be a single layer or multiple layer circuit board. For example, circuit board 101 may have two, three, four, or more layers. Printed circuit board 101 may be flexible. Persons skilled in the art will appreciate that a flexible circuit board may be at least partially or fully wrapped around or contorted around one or more objects (e.g., one or more working spaces for sterilization by the UV-C LEDs of board 101). Persons skilled in the art will appreciate that flexible circuit board 101 may utilized for multiple sterilization devices as flexible circuit board 101 may be able to flex around one or more objects (e.g., one or more hollow cylinders in which working material may be sterilized by UV-C LEDs) or may not be flexed and may lie flat next to an object (e.g., a surface of an object desired to be sterilized). Flexible circuit board 101 may be actuated so it can be flexed around different objects or placed next to an object so one device may be used in different configurations to change the location of elements of circuit board 101 to sterilize different objects and/or surfaces.

Circuit board 101 may include multiple rows and columns of UV-C LEDs and each UV-C LED, row of UV-C LEDs, and/or column of UV-C LEDs may be, for example, independently controlled (e.g., by processor 106 via additional circuitry such as additional circuitry 107). Circuit board 101 may include, for example, rows of three (or more) UV-C LEDs and columns of five (or more) UV-C LEDs). Persons skilled in the art will appreciate that rows may include the same number of UV-C LEDs or a different number of UV-C LEDs than other rows. Persons skilled in the art will appreciate that columns of UV-C LEDs may include the same or different number of UV-C LEDs than other columns. A row of UV-C LEDs may have, for example, six UV-C LEDs so that if circuit board 101 is rolled around a tube in a particular manner that the UV-C LED row provides a hexagonal disc around that tube. Each column may then, for example, provide another hexagonal disc of UV-C LEDs.

Persons skilled in the art will appreciate that circuit board 101 may be folded to provided UV-C LEDs facing in two (or more directions), left unfolded so the UV-C LEDs face in a single direction, wrapped around an object so the UV-C LEDs face into the object, folded inside of an object (e.g., a tube) so the UV-C LEDs face outside of the object, wrapped around an object (e.g., a brontoscopy or proble) with the UV-C LEDs facing away from that object, or in any form to provide UV-C LED light to any object or objects. Persons skilled in the art will appreciate that circuit board 101 may have UV-C LEDs on a single side of board 101 or multiple sides of board 101.

Cross section 110 shows a cross-section of flexible circuit board 113 including UV-C LEDs 114 and 115 inside of a tube having an interior surface 112 and an exterior surface 111. Such a tube may be cylindrical in shape or may have a non-cylindrical shape. Any UV-C material utilized with a sterilization device may be UV-C transparent and may have UV-C transparency greater than fifty percent (50%), greater than seventy percent (e.g., 70%), greater than eighty percent (80%), or greater than ninety percent (e.g., 90%). Such a UV-C transparent material may be, for example, quartz. Cross section 110 may, for example, include a cross section that includes two or more UV-C LEDs such as three or more UV-C LEDS or six or more UV-C LEDs. Persons skilled in the art will appreciate that cross-section 110 may be provided such that a flexible circuit board having UV-C LEDs is inserted into a rigid or flexible tube that is UV-C transparent to be placed in a cavity of a living organism (e.g., a nasal, throat, or lung cavity) or wrapped around or a part of a structure (e.g., a bronchoscope, nasapharangeascope, or another type of scope) in order to sterilize material placed about the tube having outer surface 111 and inner surface 112 from contaminants (e.g., viruses). Persons skilled in the art will appreciate that a thinner thickness between inner surface 111 and 112 of any tube used in connection with a sterilization device may provide more UV-C light to penetrate through inner wall 11 and 112 to interact with a working material. Accordingly, the thickness between inner surface 111 and 112 may be, for example, at or between half a millimeter and four millimeters (e.g., at or between half a millimeter and two and a half millimeters such as at or between a millimeter and two millimeters). For example, the thickness of a UV-C transparent material may be approximately two millimeters in thickness.

Side view 140 shows a side view of a cylinder with a flexible circuit board having UV-C LEDs wrapped around the cylinder. More particularly, side view 140 includes flexible circuit board 141 wrapped around a cylinder that has multiple UV-C LEDs such as UV-C LEDS 142, 143, 144, and 145. UV-C LEDs and 143 may be part of a UV-C disc that includes three or more UV-C LEDs. For example, the far side (not shown) of side view 140 may include a single UV-C LED aligned with UV-C LED 142 and 143 to provide a three UV-C LED disc around a hallow cylinder when placed around a hollow cylinder. UV-C LEDs may be facing into the hollow cylinder to provide UV-C light into a working area inside of the hollow cylinder in order to interact (e.g., sterilize) material (e.g., virus) in and/or moving through that working area. UV-C LED 142 may be aligned with UV-C LED 144 and UV-C LED 143 (and other UV-C LEDs) may be aligned with 145 (and other UV-C LEDs), respectively, so that the UV-C LEDs of multiple discs and/or rows are aligned with each other when wrapped around an object.

Cross-sectional view 120 shows circuit board 123 that may include one more UV-C LEDs (e.g., UV-C LED 124) located around a UV-C transparent hollow cylinder provided by interior wall 121 and exterior wall 122.

Cross-sectional view 130 shows circuit board 131 located around a hollow cylinder that included an interior wall 132 and an exterior wall 133. Circuit board 131 may have one or more UV-C LEDs (e.g., UV-C LEDs 134 and 135).

Side view 150 shows flexible circuit board 152 wrapped around a hollow cylinder such that LED discs are formed that are staggered from one another. For example, UV-C LED 153 may be associated with two ore more UV-C LEDs located on the far side of the cylinder while UV-C LEDs 152 and 154 may be associated with one or more UV-C LEDs located on the far side of the cylinder. Each UV-C LED disc may have the same (or different) number of UV-C LEDs but, for example, these UV-C LED discs may be staggered such that material flowing through the cylinder at different locations may have staggered UV-C LEDs that may be closer to the material than if the UV-C LEDs were not staggered with respect to one another. Persons skilled in the art will appreciate that multiple UV-C discus, rows, or columns may be staggered in two or more configurations 9 e.g., three or more configurations) and multiple groups of UV-C LEDs may be staggered differently than different groups of UV-C LEDS.

Device 160 shows a stepped hollow cylinder 162 that has three circuit boards, each having multiple UV-C LEDs wrapped around different portions of the stepped hollow cylinder. For example, circuit boards (e.g., circuit board 101 of FIG. 1) may be placed (e.g., wrapped around) portions 162, 163, and 164. Persons skilled in the art will appreciate that multiple circuit boards (e.g., circuit board 101 of FIG. 1) may be independently controlled via the same of different firmware on each board. Multiple circuit boards may be coupled to a processor and/or circuit board located outside of the boards with UV-C LEDs. A circuit board with UV-C LEDs may act as a master control circuit board to another circuit board with UV-C LEDs that acts as a slave circuit board such that the master control circuit board controls the slave circuit board.

Cross-sectional view 170 includes circuit board 173 around a hollow cylinder including interior wall 171 and exterior wall 172. The cylinder, as in any structure that is provided to include a working space in that structure, may be UV-C transparent. Circuit board 173 may include one or more UV-C LEDs (e.g., UV-C LED 176) that faces into the walls 171 and 172 such that UV-C light from UV-C LED 176 passes through walls 172 and 172 to impact the working space provided by wall 171. A material, e.g. air, may be flowed through the working space provided by wall 171 so that UV-C LEDs may impact (e.g., sterilize) that material from contaminants (e.g., virus and/or bacteria). Persons skilled in the art will appreciate that a flexible circuit board having UV-C LEDs may be laminated into the hollow cylinder itself (e.g., between walls 171 and 172. Such a configuration may, for example, provide UV-C LEDs closer to the working space. A fan, or other material movement system, may be provided to impact the speed that material is moving through the working space.

Post 175 may be UV-C transparent and may include UV-C LED 174. Configuration 181 may be provided in place of UV-C 174 and may include multiple UV-C LEDs. Any UV-C LED may be tilted at an angle on any axis in order to provide UV-C LED light in any direction. UV-C LEDs 182, 183, 184 may be provided on structure 185 and may be tilted differently on one or more axis from each other).

UV-C LEDs 174 or any UV-C LED located outside of a circuit board (e.g. circuit board 173) may be communicatively coupled (e.g., coupled by a physical conductor) to circuit board 173 so that circuit board 173 may control one or more UV-C LEDs located outside of circuit board 173.

A working space may be any working space in any device such as a ventilator device. In providing UV-C sterilization in a ventilator device any air flowing through that ventilator device (e.g., air entering, flowing through, or exiting) the device may be sterilized.

Figure 2:
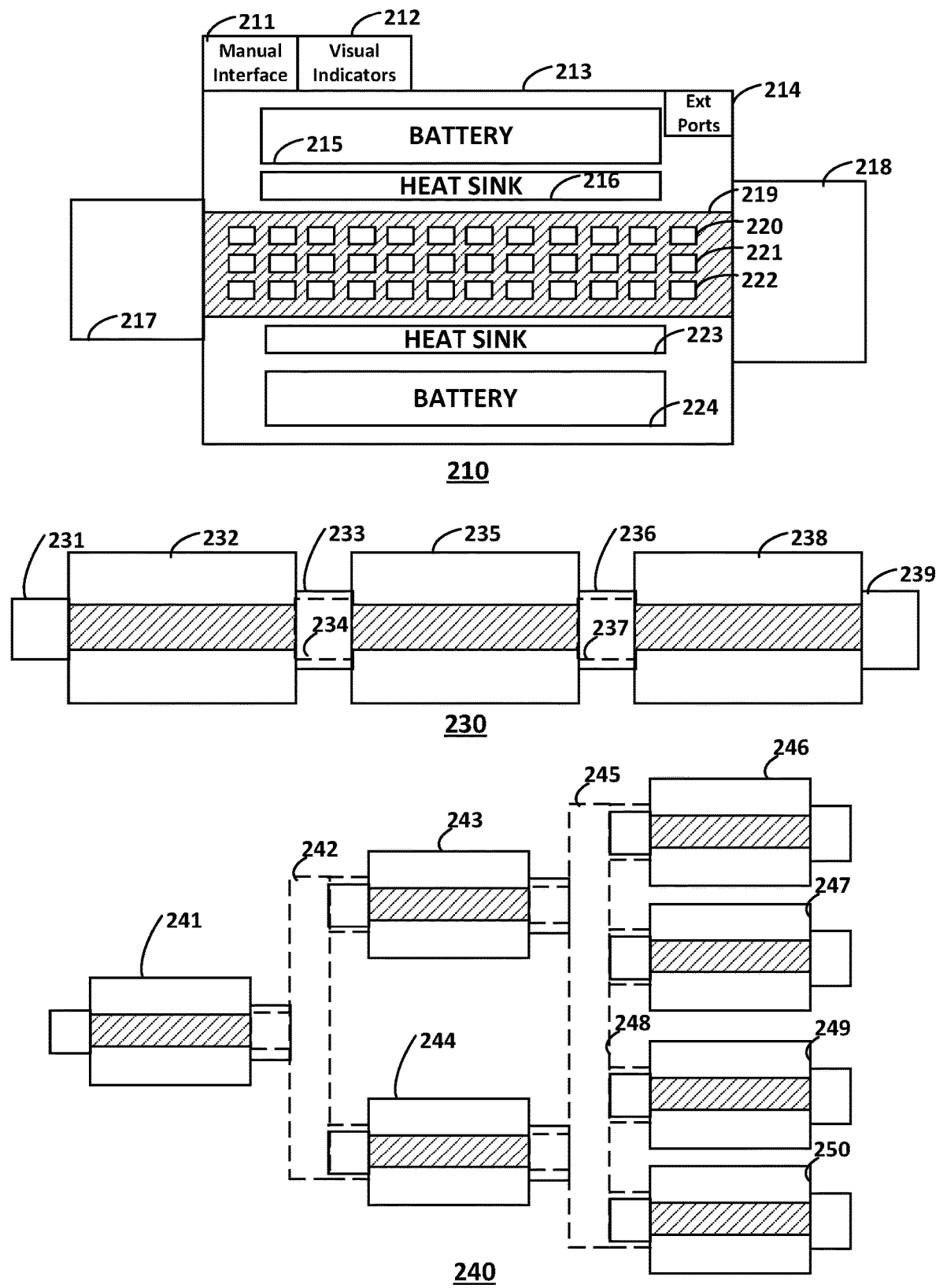
FIG. 2 are illustrations of UV-C devices constructed in accordance with the principles of the present invention.

FIG. 2 shows device 200 that may include housing 213. A hollow cylinder may be fluidically coupled to mateable portion 217 and mateable portion 218 so that a working substance (e.g., air in a ventilator) may pass through mateable portion 217, through the cylinder, and through mateable portion 218. Mateable portion 217 may be a male mateable part that fits into female mateable part (e.g., mateable part 218 may be a female mateable part). In doing so, tubing used in, for example, medical devices such as ventilators may be coupled to mateable portion 217 and 218 such that a working substance flowing through the ventilator is temporarily redirected through device 210. Circuit board 219 may include UV-C LEDs (e.g. UV-C LEDs 220, 221, and 222) around a cylinder that circuit board 2019 is wrapped around). One or more heat sinks (e.g., heat sinks 216 and 223) may be wrapped around a portion or all of circuit board 219 to draw heat generated from circuitry and UV-C LEDs away from the working space (e.g., the space inside of the cylinder). The cylinder may be a UV-C transparent material (e.g., quartz) and may include a thickness between an inner wall and an outer wall between approximately 1.5 millimeters and 2.5 millimeters (e.g., approximately 2 millimeters). Persons skilled in the art will appreciate that heat sink 210 and 223 may be a single heat sink wrapped around circuit board 219 wrapped around a hollow cylinder (or other structure providing a working space). Persons skilled in the art will appreciate that a cylinder or other structure may not be provided and circuit board 219 may define the working space itself. For example, circuit board 2019 may be wrapped into a cylinder and a working material may be followed through that cylinder. A protective layer may be placed (e.g., sprayed or placed) on one or more portions of one or more surfaces of the circuit board to provide protection for the circuit board from any working material.

Device 210 may include one or more batteries 215 and 224. Persons skilled in the art will appreciate that batteries 215 and 224 may be separate batteries or a single battery wrapped around housing 213. Batteries may be rechargeable or permanent and removable and replaceable. Charging circuitry may be provided. External power may recharge the power or, for example, may power circuitry of device 210 directly. Switching and regulation circuitry may control, for example, when external power (e.g., wall power) is utilized to charge a rechargeable battery and/or power circuitry of device 210 directly. Manual interfaces 211 may be included such as, for example, to turn device 210 ON/OFF and or change modes or enter other input data into device 210 (e.g., configure device settings and or device modes). Visual indicators 212 may be a bi-stable or non bi-stable display and/or single-color light source(s) and/or multiple color light source(s). A visual indicator may be a two-color display (e.g., black and white or two tone display) or a several color display (e.g., a color display) and may include an interface for the consumer. Visual indicators 212 may include the status of device 210 Status may include, for example, status information such as, for example, whether device 210 is operating properly or incorrectly as well as data associated with the device. For example, device 210 may provide a visual indication of a low battery, broken part (e.g., broken UV-C LED). Audio indicators may also be provided such as speakers. Audio and/or visual information may be provided such as, for example, when a battery is less than a particular amount of charge (e.g., less than twenty percent or less than ten percent of charge) or when a software update is available. External ports 214 may be provided anywhere on housing 213 such as on mateable port 217 and 218 such that external power and/or control and/or data input/output may be provided. By including external ports 214 on mateable portions multiple devices can be physically coupled together and the coupled devices may communicate to each other (e.g., control and power each other). Any number of devices

210 may be coupled to one another to, for example, provide a multiple or several device array or, for example, to increase the sterilization impact on a working substance. Two or more devices 210 may be coupled to a ventilator. Two or more devices 210 may be coupled to different parts of a ventilator or may be coupled adjacently to a single part of a ventilator.

Devices 230 are provided that include device 232 having mateable portions 231 and 233, device 235 having mateable portions 234 and 236 and device 328 having mateable portions 237 and 239. A working substance can be flowed (e.g., pushed and/or pulled) through an opening in mateable portion 231 and through devices 232, 235, and 238 to be expelled through an opening in mateable portion 239.

Devices 240 may be provided and may include devices 241, 243, 244, 246, 247, 248, and 250. Adaptors 242 and 225 may be included to create a joined working space between any number of devices. Adaptor 242 may, for example, fluidically couple device 241 to device 243 and 244. Adaptor 245 may, for example, fluidically coupled devices 243 and 244 to devices 246, 247, 249, and 250.

Figure 3:
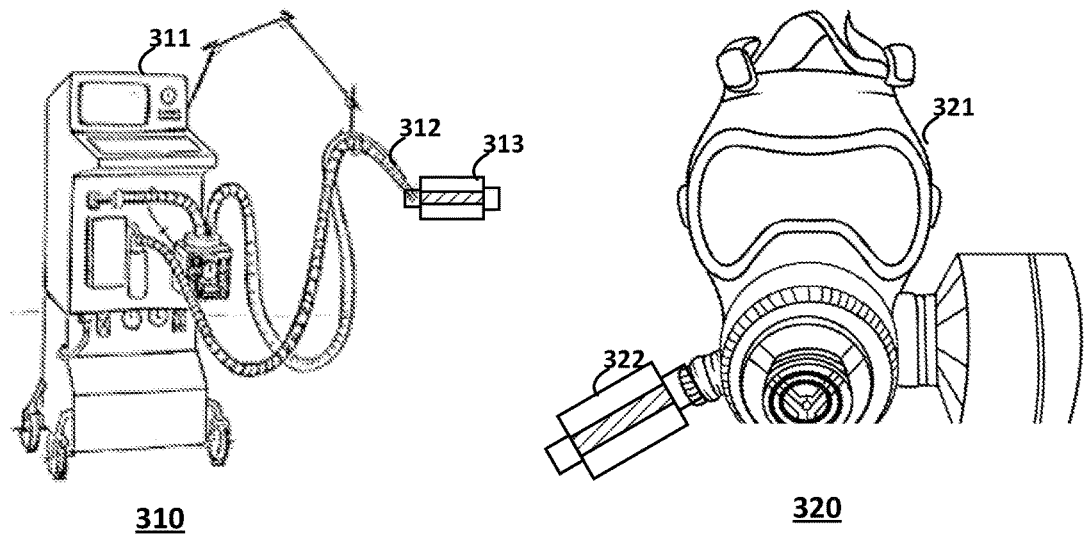
FIG. 3 are illustrations of UV-C devices constructed in accordance with the principles of the present invention.
Figure 3:
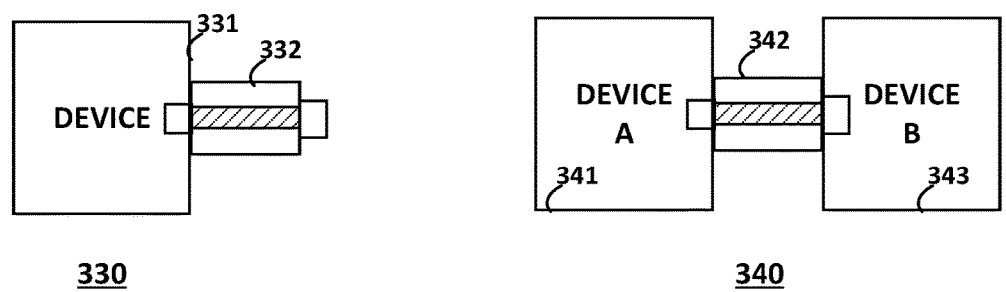
Figure 3:
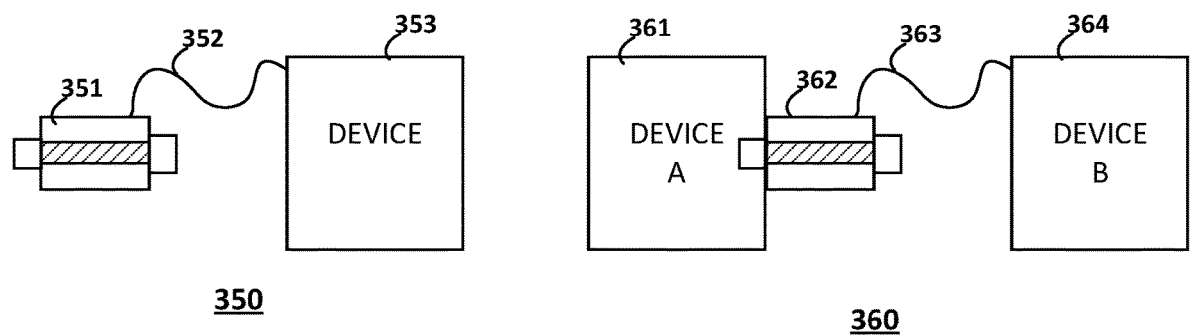

FIG. 3 shows ventilator 310 that may include housing 311 tubing 312 and device 313 that may include device 313 for providing UV-C light to the working substance provided by tubing 312. Deice 313 may be, for example, any UV-C generating device included herein such as, for example, device 100 of FIG. 1.

Persons skilled in the art will appreciate that a UV-C generating device may have liquid and/or gas flowed through it from any structure. Accordingly, for example, a UV-C sterilization device may be placed about an input and/or output and/or filter port to any device such as a face mask. Accordingly, for example, a face mask wearer (e.g., a military, police, firefighter, caregiver) may enjoy improved protection against contaminants (e.g., bacteria and/or virus). Configuration 320 may be provided that may include UV-C sterilization device 322 fluidically coupled to an air channel of mask 321. Persons skilled in the art will appreciate that multiple UV-C sterilization devices may be coupled to one or more air channels of mask 321.

Configuration 330 of FIG. 3 shows device 331 coupled to UV-C generating device 332. Device 331 may be, for example, an substance cooler, substance heater, substance fan, and may be fluidically coupled to provide the substance worked on, expelled, or input into device 331 through device 332 to provide, for example, sterilization capability.

Configuration 340 may be provided any may include device 341 fluidically coupled to device 343 through UV-C generation device 342 such that a substance moved between device 341 and 343 may be sterilized by, for example, device 342.

Configuration 350 may include device 353 communicatively coupled to UV-C generating device 351 via physical or wireless communications 353 such that information and controls may be provided between device 353 and device 351.

Configuration 360 may be included that includes device 353 fluidically coupled to device 261 and communicatively coupled to device 264. Device 264 may also be communicatively coupled or fluidically coupled to device 261. Persons skilled in the art will appreciate that device 362 may be communicatively coupled to multiple or several other devices as well as fluidically coupled to multiple or several other devices.

Figure 4:
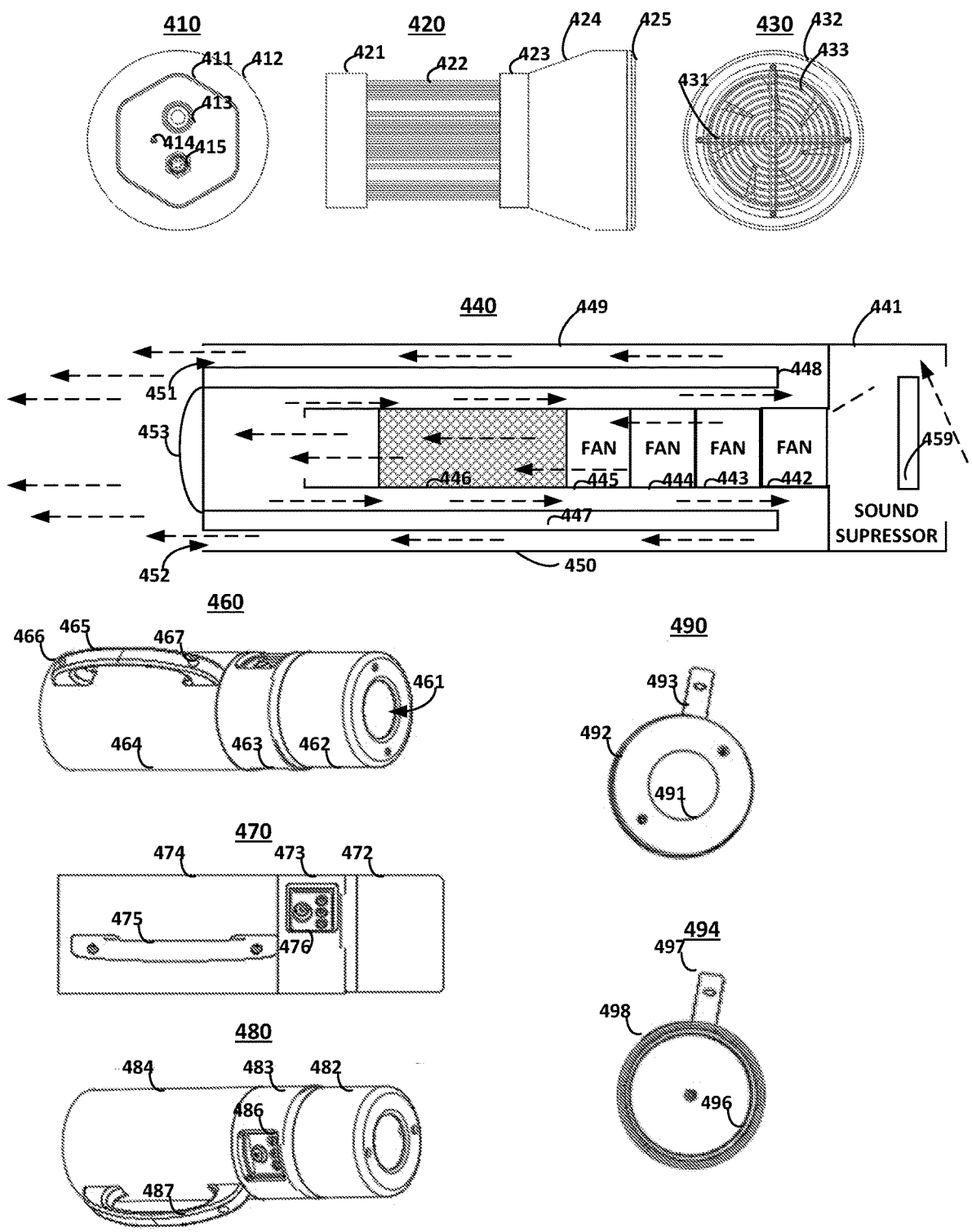
FIG. 4 are illustrations of UV-C devices constructed in accordance with the principles of the present invention.

FIG. 4 shows air sanitization device 410 which may have fan portion 412 and control portion 411 that may include several state switch 414, button 413, and power connection 415. Persons skilled in the art will appreciate will appreciate that several state switch 414 may, for example, a switch that has more than two states. Switch 414 may be, however, a switch that has two states. Button 413 may be a two state switch but may also have more than two states. Air sanitization device 410 may, for example, be utilized to sterilize materials other than air. For example, air sanitization device may be utilized to sterilize a liquid (e.g., water, blood, bodily fluid, or a non-bodily fluid. Device 410 may be, for example, a side view of device 410 and may include control portion 421, fan portion 424, UV-C working area portion 422, mechanical grill 425, and extension portion 422. Air, or another substance, may, for example, be brought into fan portion 424 by one or more fans provided in fan portion 424. Mechanical grill 425 may, for example, include mechanical structures to permit air to flow past the mechanical structures, but that may prohibit structures beyond a particular size from entering fan portion 424 so the fan(s) are not damaged. Similarly, mechanical grill 425 may protect a person from putting their hand into fan portion 424 so that the person does not get accidently harmed while operating the UV-C air sanitization device.

Persons skilled in the art will appreciate that UV-C working area portion 422 may include an area where UV-C is introduced to the substance flowing through device 422 for sterilization. Such an area may be provided, for example, by a structure such as a tube made of UV-C reflective material (e.g., a PTFE material with at least 90% reflectivity or 95% reflectivity). Apertures may be cut into the structure and one or more UV-C light emitting diodes may be provided in the apertures. UV-C transparent material may be provided in the apertures, for example, such that the UV-C light emitting diodes provide light through the UV-C transparent material and into the working area and the UV-C light may reflect off the UV-C reflective material and be retained, at least partially, in the working area. Persons skilled in the art will appreciate that UV-C transparent material may be, for example, a quartz with at least 85% UV-C transparency or at least 90% UV-C transparency. UV-C LEDs may be provided, for example, with UV-C between 100 nm and 280 nm (e.g., between, and including, 200 and 280 nm or between, and including, 260 nm and 270 nm).

UV-C working area portion 422 may include heat sink and heat sink fins that are thermally coupled to one or more UV-C light source(s) (e.g., LED(s)) and permit air to flow past the heat sink and heat sink fins and remove heat from the heat from the device. Persons skilled in the art will appreciate that a substance (e.g., air) may be brought through fan portion 424 through a structure such as a cylinder and UV-C may be applied into this cylinder and then the treated air may be stopped from exiting the device by interface portion 421 and then air may flow back outside the cylinder past heat sinks and/or heat sink fins and then may exit the device, for example, about extension portion 423. Persons skilled in the art will appreciate that UV-C treated air may be heated by heat sinks and heat sink fins and this heat may perform additional sanitization of certain types of contaminants that are reactant to heat (e.g., virus such as SARS-CoV-2).

Device 430 may be, for example, a view facing a fan portion of a device (e.g., fan portion of device 420) and may include fan portion 432 with grill structures 433 and 431.

Persons skilled in the art will appreciate that a UV-C working area may be provided by a cylinder or other hollow structure such as a spherical cylinder, elliptical cylinder, rectangular cylinder/prism, square cylinder/prism, triangular cylinder/prism, or any other shape channel including channels that may change shape as the channels progress in a direction. UV-C LEDs may be provided on a flexible printed circuit board that is flexed around a cylinder (e.g., a quartz cylinder) and mounted to the cylinder and/hour housing (e.g. through screw apertures located on the printed circuit board). Any number of rows and columns of UV-C LEDs may be provided and these rows and/or columns may be aligned and/or staggered for entire columns and/or rows or portions of columns and/or rows.

One or more heat sinks may be provided, for example, on the back of a flexible circuit board so that heat from a UV-C LED may travel from the UV-C LED through the circuit board to one or more heat sinks. A heat sink may be for example, aluminum and/or copper (e.g., copper inside of the aluminum to improve flow of heat through the aluminum). Thermal paste or another thermal substance may be utilized to improve thermal coupling of a portion of a device (e.g., back of circuit board under a UV-C LED) with a heat sink. One, two, or several Heat dissipation fins, such as fins 402 and 419, may be provided and may be provided as part of or coupled to one or more heat sinks. Persons skilled in the art will appreciate that batteries may be provided in air sanitization houses.

An air sanitization device may be provided in which an object may be passed through one or more UV-C working area(s). Different types of UV light sources (e.g., tube lamps) and different types of UV light (e.g., UV-A and/or UV-B devices) may be provided to provide various types of UV light into a UV working area.

Persons skilled in the art will appreciate that a UV-C generation device may have any number of UV LEDs of any number of types and wavelengths and be provided in any configuration and density. Multiple devices may be fluidically coupled together o so that the sterilization capability may be increased by creating additional UV-C working areas that are fluidically coupled together (e.g., the output of an air sanitization device is coupled to the input of an air sanitization device.

A UV-C working area defining structure (e.g., tube) may be provided at a slant with respect to a base. In providing a slant, UV light (e.g., UV-C light) may be directed away from an opening so that UV-C light does not pass through the opening (e.g., the entrance). Different mating structures may be provided about input and/or output outlets of an air sanitization device so that the air sanitization device may be, for example, coupled to an external device such as a ventilator for air sterilization.

A conveyer or moveable tray or pushing object may be utilized to move an object through a working channel. Persons skilled in the art will appreciate that structures may be provided in a UV working area to slow down an object and or direct an object in a certain direction in order to, for example, increase the time of an object in a working channel. For example, a working channel may include multiple turns in order to, for example, potentially decrease the speed of objects flowing through a working channel.

Persons skilled in the art will appreciate that the entrance and/or of a UV working area may take any dimension and shape, may take the same dimension and/or shapes, and/or may take different dimensions and/or shapes. Furthermore, persons skilled in the art will appreciate that a UV working area may have multiple entrances and multiple exits (and may be bi-directional do objects can enter from any exit and enter through any exit). The working area channel may have the same dimensions or different dimensions as an opening. Multiple or several connected and/or independent UV working areas may be provided in a device.

An opening to a UV-C working area may, for example, have any length and/or width. For example, the width of an opening may be less than, greater to, or equal to 0.5 inches, 1.0 inches, 1.5 inches, 2.0 inches, 2.5 inches, 3.5 inches, 6 inches, 12 inches, 18 inches, 24 inches, etc. For example, the length of an opening may be less than, greater to, or equal to 0.5 inches, 1.0 inches, 1.5 inches, 2.0 inches, 2.5 inches, 3.5 inches, 6 inches, 12 inches, 18 inches, 24 inches, etc. For example, the width of an opening may be less than 6 inches and the length of an opening may be less than 24 inches.

Device 440 may include sound suppressor 441 in which air is brought into a sound suppression chamber to block sound coming from fans 442-445 toward the direction of the inlet of the sound suppressor. Sound suppressor may include one or more inlet sound barriers 459 that may be fabricated from a plastic (e.g., a 3D printed plastic and/or a molded plastic). A soundproofing material (e.g., a soundproofing foam) may be provided in the device between fan 442 and structure 459.

Fans 442-445 may be provided in any number of structures. For example, Fans 442 and 443 may be provided in one structure and fans 444 and 445 may be provided in a second structure. Each pair of fans may be, for example, count-rotating compression fans or may be non-compression fans. Each pair of counter-rotating fans may be, for example, synched together or may be offset from one another. Fans may be utilized to push air through a device and/or pull air through a device (e.g., during different operating modes). A UV-C working area may be provided as area 446 which may be defined, for example, by a UV-C reflective structure such as a UV-C reflective tube. Apertures may be provided in the tube for UV-C light sources (e.g., UV-C LEDs) to be included through one or more circuit boards (e.g., flexible circuit boards) or other structures. Transparent windows may be placed between the UV-C LEDs and the working area so that working area substances (e.g., air) does not touch the UV-C LEDs. Such windows may be UV-C transparent (e.g., a quartz or other UV-C transparent material). Heath sinks (e.g., copper heat sinks) and heat sink fins (e.g., aluminum heat sink fins or copper heat sink fins) may be utilized to remove heat from UV-C LEDs. UV-C inactivated air from working area 446 may be routed out of the UV-C inactivation chamber and returned over the exterior of a structure providing working area 446 (e.g., through heat sinks and heat sink fins removing heat from UV-C light sources providing UV-C light in working area 446). In doing so, for example, inactivated air may be utilized to, for example, also cool the device by removing heat from the heat sinks. In doing so, for example, only inactivated air may be moved out of the device. In doing so non-inactivated air is not moved out of the device so virus in non-inactivated air may not be spread by the device. Furthermore, inactivated air that is removing heat may be routed again via routing structures 447 and 448 so that air is routed at an end opposite an inlet (e.g., via outlet channels 451 and 452. In doing so, the chance that outlet air is re-introduced to an inlet of the device may be reduced. Furthermore, curved surface 453 (e.g., which may be a convex surface) may tighten and increase the throw of air from outlet channels 451 and 452. For example, air being introduced into device 440 at fans moving air at, for example, 400 liters per minute or higher may, for example, provide a throw (e.g., a distance air moves from the device in a human perceivable manner) by at least six feet from outlets 451 and 452. Housing structure 449 and 459 may be a metal, which may increase sound absorption, and then have a plastic casing outside of that metal, which may reduce the amount of heat a user feels if the person touches the outside of housing structure 449 and 459. Structures 448 and 447 may be a metal (e.g., an aluminum). Structure 453 may be, for example, a plastic (e.g., a 3D printed or molded plastic).

Device 460 may include inlet 461, sound suppressor 462, control section 463, housing structure 465, removable handle 465, and removable handle screws 466 and 467. Person skilled in the art will appreciate, for example, that device 460 may includes one or more components as device 440 of FIG. 4

Device 470 may include sound suppressor section 472, interface section 473, and housing section 474 and may include removable handle 475. Persons skilled in the art will appreciate that section 473 may be a plastic (e.g., a 3D printed and/or molded plastic) and may include an aperture exposing an interface. Such an interface may have one or more buttons (e.g., a toggle button) and one or more user perceivable visual indicators (e.g., three visible light sources of the same or different colors). Device 470 may be a different perspective view of device 460 of FIG. 4.

Device 480 may be a different perspective view of device 470 of FIG. 4. Device 480 may include sound suppressor section 482, interface section 483 with interface access aperture 486, removable or fixed handle 487, and housing structure 484. Air may be introduced into air suppressor 482 and may be inactivated by UV-C light sources in device 480 and moved out of the device at the end of housing structure 484.

Device 490 may be a front perspective view of device 460 of FIG. 4 and may show inlet aperture 491, sound suppressor structure 492, and handle 493.

Device 494 may be a rear perspective view of device 460 and may include outer edge 498 and inner edge 496 and air may be ejected from device in the space between outer edge 498 and inner edge 496.

Figure 5:
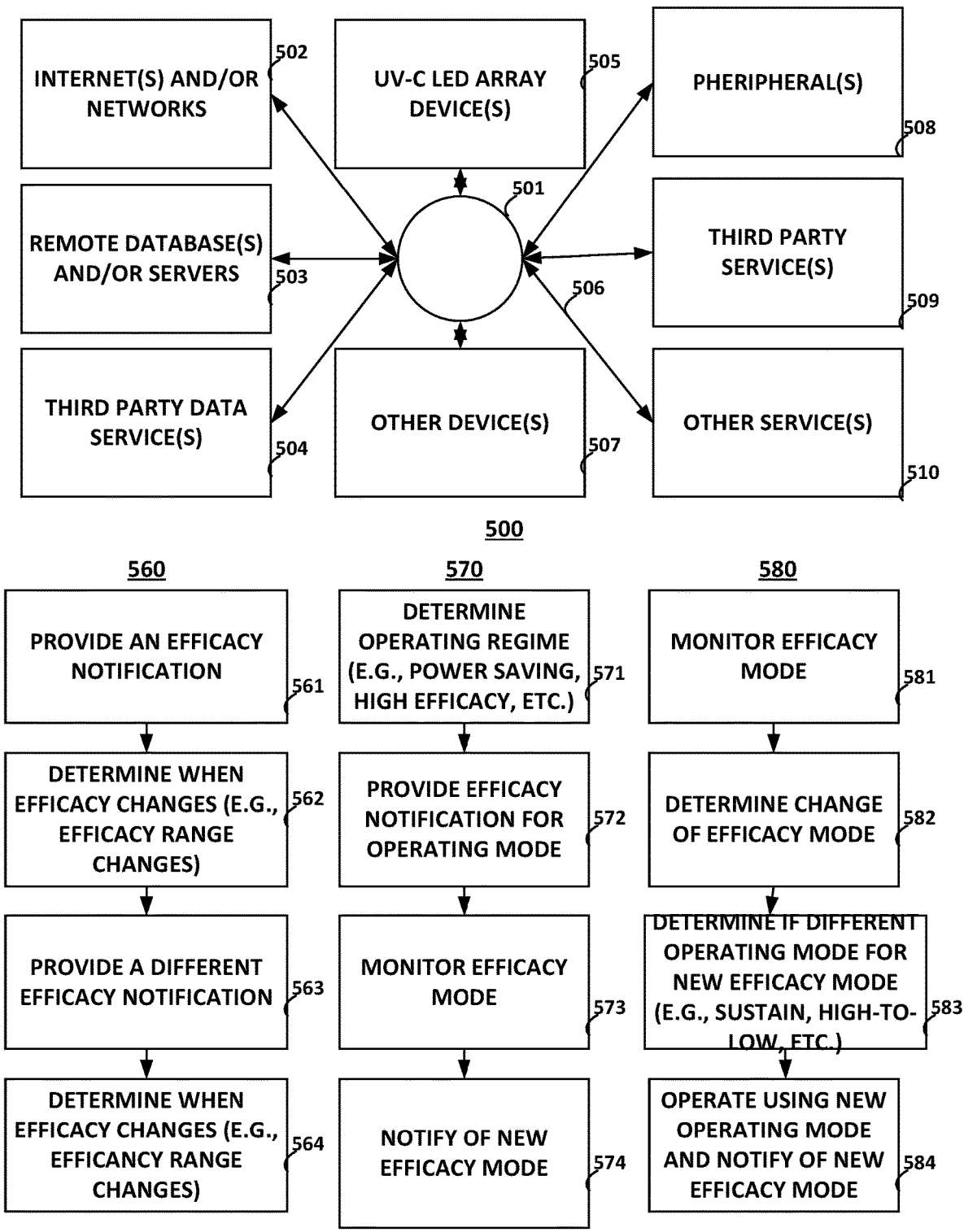
FIG. 5 are illustrations of flow charts constructed in accordance with the principles of the present invention.

FIG. 5 shows topology 500 that may include UV-C generating devices 205 that may include one or more UV-C arrays of LEDs coupled through communications 501 to one or more internets and/or networks 502, one or more remote databases and/or servers 503, one or more third party data services 504 (e.g., medical data services for a patient utilizing a UV-C generating device), one or more other devices 507 (e.g., one or more other medical devices for a patient using a UV-C generating device), one or more other services 510 (e.g., a service that provides data regarding other UV-C generating devices), one or more third party services 509 (e.g., timing/clock services for the timing/clock of a UV-C generating devices), and/or one or more peripherals 508 (e.g., external displays, external batteries).

Persons skilled in the art will appreciate that UV-C generation devices may be utilized for surface sanitization such as sanitization of organic or inorganic material.

Process 560 may be associated with a UV-C inactivation device such as a UV-C air inactivation device for inactivating one or more virus (e.g., SARS-CoV-2). An efficacy notification may be provided in step 561 (e.g., of a device or system operating at a particular efficacy level such as an efficacy range), efficacy level may have bene determined to have changed in step 562 and a different efficacy notification may be provided in step 563. A device, or system, may then determine when efficacy changes (e.g., efficacy range changes) in step 564 (e.g., and provide an additional notification). Person skilled in the art will appreciate that when one or more light sources (e.g., UV-C light sources) are exhausted a consumer may be notified that the light sources may need to be changed. Persons skilled in the art will appreciate that multiple fault modes may be provided such as, for example, if a power supply is determined to potentially be damaged, fans are determined to potentially be damaged, etc. In providing fault codes or other such notifications of damage events, a consumer or a technician may more easily diagnose and issue and remedy the issue (e.g., purchase a new power supply). A UV-C generating device may be utilized with a wall plug through, for example, a power supply.

Process 570 may be included and may include step 571, in which an operating regime (e.g., a power saving or high efficacy) is determined (e.g., via an autonomous control or a manual control (e.g., a button such as a two state switch). Efficacy notification for the operating mode may be provided in step 572. The efficacy mode may be monitored in step 573 and a new efficacy mode may be determined and a notification provided in step 574.

Process 580 may utilize step 581, in which an efficacy mode may be monitored. A change of efficacy may be determined in step 582. A determination may be made in step 583 to determine if a new operating mode is utilized for a new efficacy mode (e.g., sustain efficacy at a point or operate to let efficacy decrease over time) in step 583. Operation using a new operating mode and notification of a new efficacy mode may be provided in step 584.

Figure 6:
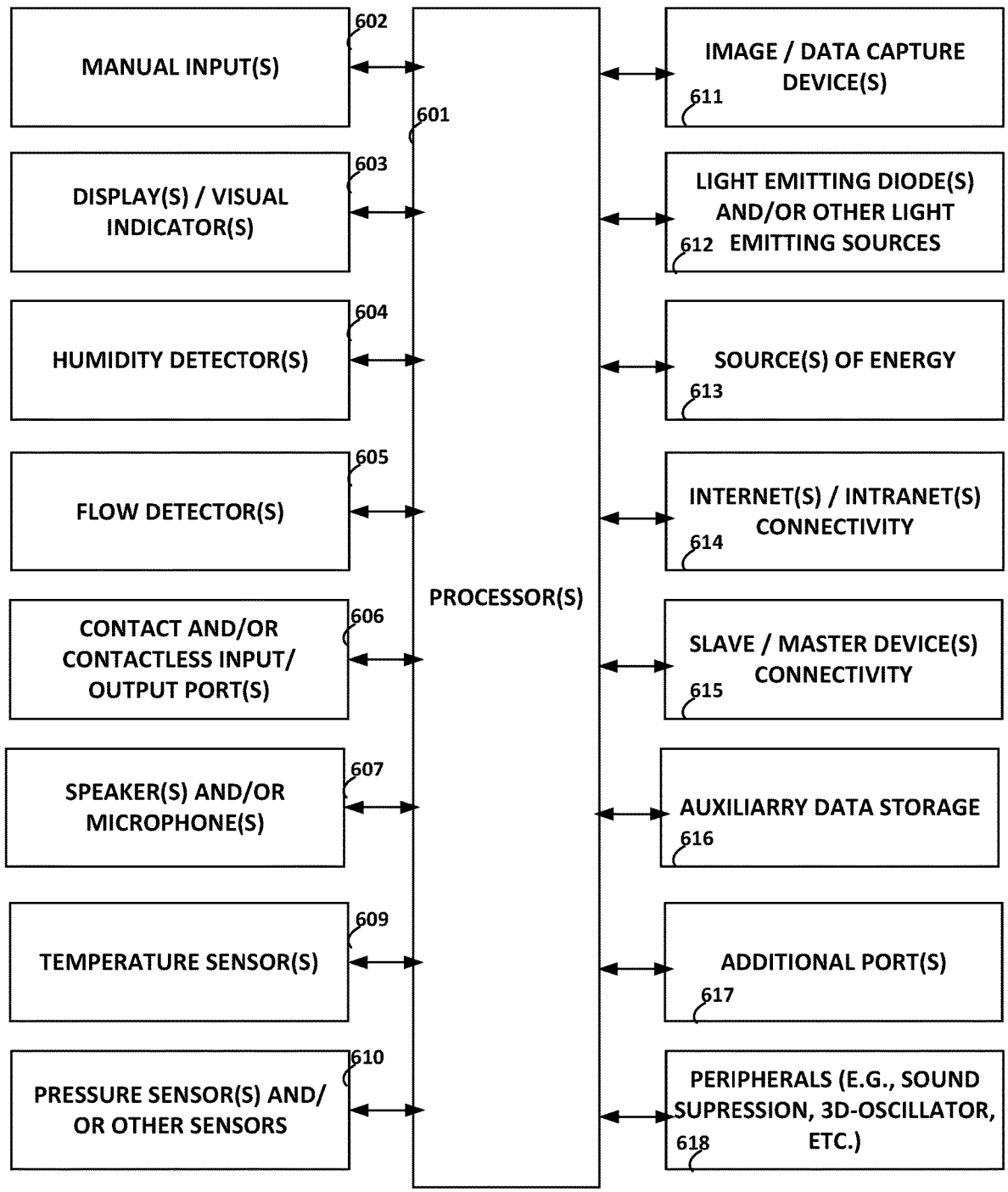
FIG. 6 is an illustration of UV-C device constructed in accordance with the principles of the present invention.

FIG. 6 includes device 600 that may include one or more processors 601, one or more manual inputs 602, one or more displays and/or visual indicators 603, one or more humidity detectors 605, one or more flow detectors 605, one or more contact and/or contactless input and/or output ports 606, one or more speakers and/or microphones, one or more temperature sensors 6o*i* (e.g., to sense temperature in a working space), one or more pressure sensors 610 (e.g., pressure sensing for sensing pressure in a working space) and/or other sensors (e.g., metal sensors UV-C transparency sensors), one or more image and/or data capture devices 610 (e.g., a visible and/or infrared or other spectrum camera or data capture device), one or more light-emitting diodes and or other light emitting sources 612 (e.g. UV-C LEDs and/or UV-C light emitting sources), one or more sources of energy 613 (e.g., rechargeable and/or removable batteries), one or more internet or intranet connectivity devices 614, one or more slave and/or master devices 615, one or more auxiliary data storage devices 616 (e.g., a remote server), and one or more peripherals 618 (e.g., external fans that may oscillate or not oscillate in order to push air toward the sanitization device as part of a larger air movement system).

Peripheral 618 may include an oscillator, such as a two axis, three axis, or more than three axis oscillator for moving a UV-C generating device around the controllable various axis. One or more sound suppression structures, such as sound suppression cambers that air flows through, may be permanently fixed to a device and/or removably attached to a device. In doing so, for example, a user may purchase and add sound suppression structures to increase the sound suppression of the device. Multiple sound suppression structures may be mated together through mateable structures to provide additional sound suppression.

Persons skilled in the art will appreciate that any type of UV light may be utilized, for example, to create a UV inactivated vaccination and that particular strains may be inactivated with one wavelength of UV and another strain may be inactivated with a different wavelength. Such inactivated virus vaccinations may be aerosolized and may be inactivated in aerosolized forms. An aerosolized vaccination may then be, for example, changed to be in a different form (e.g., a liquid vaccination). Persons skilled in the art will appreciate that a UV-C inactivated strain vaccine may include portions of light outside of UV-C and a majority of the light (e.g., 50 percent or more, 75 percent or more, 85 percent or more, 90 percent or more, 95 percent or more, 98 percent or more, 99 percent or more, or 100 percent) may be UV-C.

Persons skilled in the art will appreciate that a UV-C inactivation device may include eighteen UV-C LEDs and may inactivate bacteriophage, a DNA virus, at 30 liters per minute at an inactivation rate greater than 99.999% at a humidity greater than 50%. Persons skilled in the art will appreciate that a UV-C inactivation device may include eighteen UV-C LEDs and may inactivate, SARS-CoV-2, a RNA virus, at 400 liters per minute at an inactivation rate greater than 99% at a humidity greater than 50%.

Figure 7:
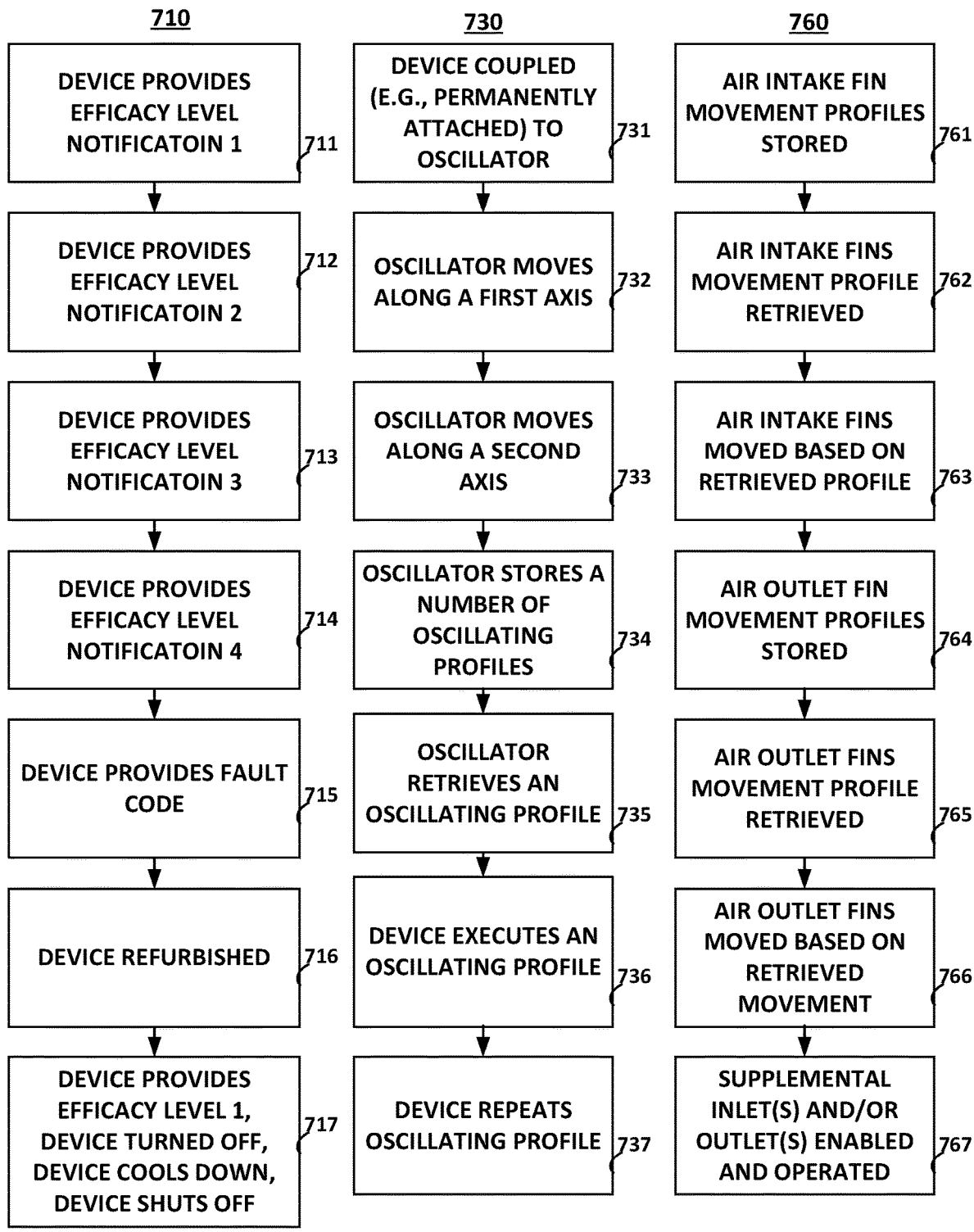
FIG. 7 are illustrations of flow charts constructed in accordance with the principles of the present invention.

FIG. 7 includes process 710 that may include step 711, which may include providing a first efficacy level notification (e.g., greater than 90% inactivation of a particular virus). Step 712 may be provided in which a second efficacy level notification is provided (e.g, 75% to 79.9% inactivation of a particular virus). Step 713 may be provided in which a third efficacy level notification is provided (e.g., 51% to 74.9% inactivation of a particular virus). Step 714 may be provided an may include a fourth efficacy level notification (e.g., lower than 51% inactivation of a particular virus). A fault code may be provided in step 715 (e.g., when UV-C LED(s) on a device are below a particular efficacy level and replacement may desired by the consumer to obtain various efficacy levels that may be no longer capable on the device. A device may be refurbished in step 716 (e.g., by obtaining UV-C LED(s) replacements) and the device may provide efficacy level 1 in step 717. A device may then be turned off in step 717 (e.g., by a consumer after operation) and a cool down mode may be provided for a particular period of time (e.g., for 1 minute) and the device may then shut off. Persons skilled in the art will appreciate that a cool down feature may be provided in which UV-C LEDs are turned OFF and fans are kept ON so that air continues to circulate through a device to cool the device down. After a particular period of time, the device may then automatically shut OFF. Person skilled in the art will appreciate that a cool down may be provided after a device has been on for a particular period of time, after a particular heat has been detected for a particular mode by a heat detector, or as a result of any event.

Process 730 may include step 731, in which a device such as an aerosolized virus inactivation device may be coupled permanently (e.g., during manufacturing in a manufacturing facility) or removably attached to an oscillator such as a one axis or two axis oscillator. An oscillator may move the aerosolized inactivation device about a first axis in step 732 and may move the device about a second axis in step 733. A number of oscillating profiles may be stored in step 734 (e.g., two, three, more than three such as more than five). An oscillating profile may be retrieved in step 735. A device may execute an oscillating profile in step 736 and may move according to that oscillating profile by moving about one or more axis at particular speeds in particular directions for particular periods of time and at particular accelerations at different times. An oscillator profile may be repeated (e.g., autonomously) in step 737 and repeated continuously until a new oscillating mode is determined (e.g., manually or autonomously such as autonomously as a result of data from one or more sensors located on the device).

Process 760 may include step 761 in which air intake fin(s) movement profiles are stored (e.g., in memory of a UV-C generating device such as a UV-C inactivation device such as a UV-C aerosolized virus inactivation device. Air intake fin movement provides are retrieved in step 762 and moved based on retrieved profiles in step 763. Air outlet fin(s) movement profiles (e.g., two, three, or more than three such as at least five) in step 764. A outlet fin movement profile is retrieved in step 765 and outlet fins are moved based on the retrieved profile in step 766. Additional inlet(s) and/or outlet(s) may be enabled and operated (e.g., opened, closed, partially opened/closed) in step 767.

An inactivation device (e.g., a SARS-CoV-2 inactivation device) may include a fan portion and working area portion. A working area portion may include, for example, a structure that provides a working area for air, or another substance, to flow through, one or more circuit boards provided about the structure that includes one or more UV-C light sources (e.g., LEDs) as well as additional electronics (e.g., microprocessors, input/output ports, additional circuitry), heat sinks and heat sink attachment structure(s) (e.g., thermal paste), heat sink fins and heat sink fins attachment structures (e.g., if the heat sink is separate from the heat sink fins such as a copper heat sink and aluminum heat sink fins), and/or a primary housing that provides a mechanical structure as a foundation for the placement of structures in a working area portion.

FIG. 8 shows tube 810 that may provide a working area for UV-C inactivation. Tube 810 may include mateable portion 811 and air opening 812. Apertures (e.g., stepped apertures to receive UV-C transparent windows, such as quartz, in the step of an aperture and fixed using an adhesive) may be provided such as aperture 813. A UV-C LED may be provided to provide UV-C light into one or more UV-C apertures on tube 810. Multiple (e.g., eighteen or more) UV-C LEDs may be provided on a flexible circuit board and wrapped and attached (e.g., via a mechanical fixation device(s) such as screw(s) or adhesive(s)) to the tube. Trough 814 may be provided to permit a circuit board to fall into trough so that UV-C LEDs may get closer to a working surface (e.g., to increase intensity and inactivation). Additional apertures (e.g., aperture 814) may be provided for sensors such as, for example, light sensors (e.g., to determine the intensity or other attributes of one or more UV-C LEDs)

Tube 814 may be, for example, a different perspective view of tube 810 of FIG. 8. Tube 815 may be fabricated, for example, completely, or partially, from a UV-C reflective material (e.g., a PTFE material) and may have UV-C reflectivity greater than 95% (e.g., greater than 95% for nanometer wavelength ranges centered at a point in the range of 250 nm and 280 nm such as centered at a point in the range of 255 nm to 270 nm such as centered at a point in the range of 255 nm to 265 nm). Tube 815 may include external surface 818, mateable portion 816, and air opening 817.

Device 820 may be, for example, a heat sink fixture for a tube (e.g., tube 810 of FIG. 8). A tube, such as tube 826 may be provided with UV-C LEDs providing UV-C light into tube 826. Heat sinks may be provided such as heat sinks 823 and 824 (e.g., copper and/or aluminum heat sinks such as a heat sink with a copper inside of the aluminum). Plates 822 and 821 may be provided to fix the heat sinks in position around a tube and may be affixed with one or more screws such as screw 825. Air channels 826 may be provided to permit air to flow. Persons skilled in the art will appreciate that air channels may be provided close to heat sinks so that air is brought close to one or more heat sinks as air flows through the device (e.g., inactivated air is flowed past the heat sinks to remove heat from the device as the inactivated air leaves the device.

Device 830 may be, for example, a different perspective of device 820 of FIG. 8 and may include heat sinks 831-833.

Any number of mounting structures may be provided on a heat sink such that the heat sink may receive any type of structure. For example, each heat sink in device 830 may receive one or more heat sink fins (e.g., aluminum fins) that may be made from the same or different material as the heat sink.

Device 835 may be, for example, a different perspective of device 830 of FIG. 3 and may include tube 838, screw 837, and air flow channel aperture 836.

Device 840 may be, for example, a structure that is included in a UV-C aerosolized pathogen inactivation device and may be, for example, plastic (e.g., 3-D printed plastic with standblasted surfaces or permanent or temporary molded plastic) or metal (e.g., aluminum). Device 840 may be utilized, for example, to house fans (e.g., two pairs of counterrotating compression fans) and to direct and concentrate air into a working channel provided by a tube (e.g., a 10 to 35 millimeter internal diameter tube such as a 15 millimeter inner diameter tube). Device 840 may include housing portion 845, funnel portion 846, attachment foot 847, flat interface surface 841, visual indicator apertures 842-844 for receiving visual indicators (e.g., visible spectrum LEDs), and manual input aperture 848 for receiving a manual input device. Any number of manual input and/or visual indicator devices may be placed about any portion of any surface of any device such as device 840.

Figure 8:
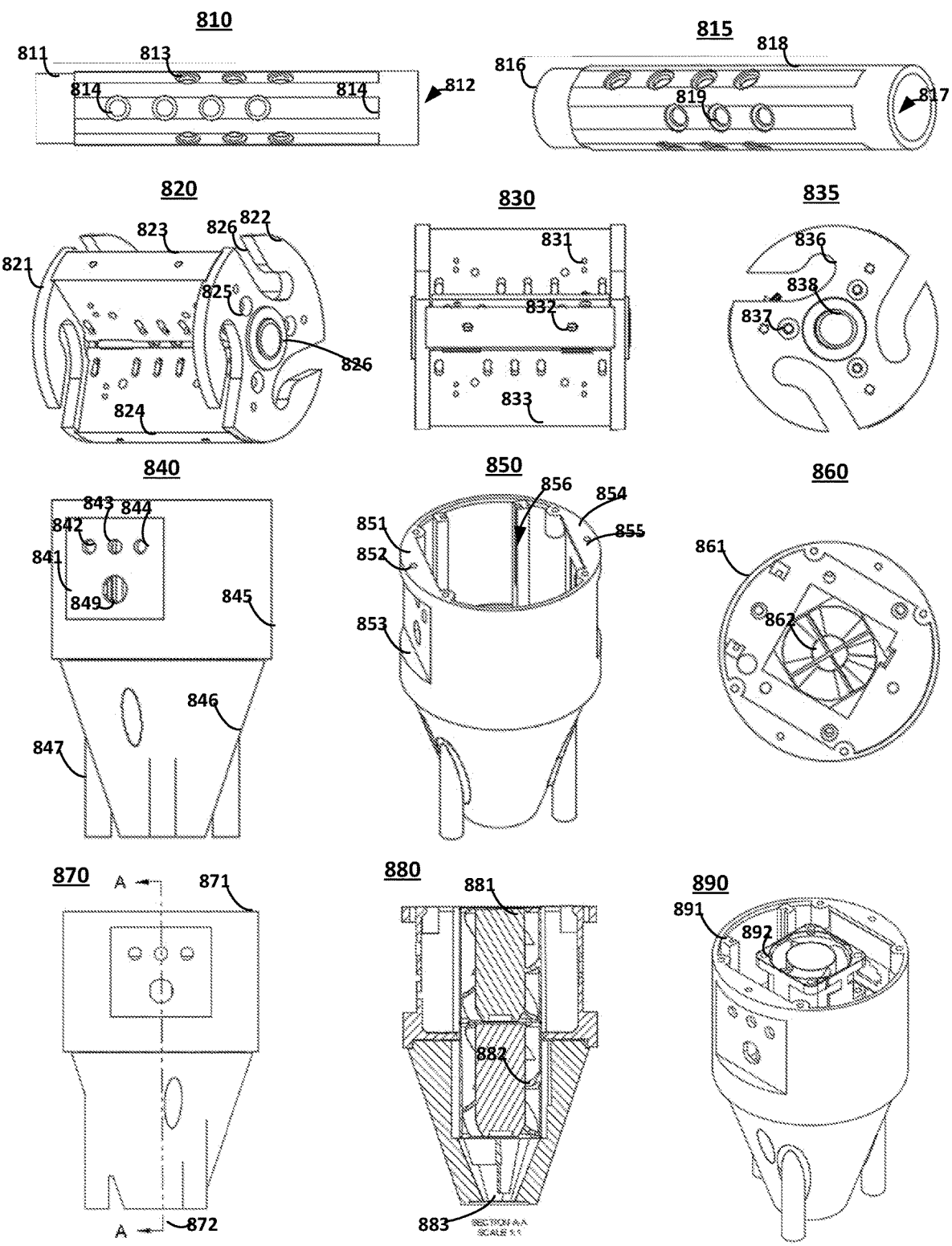
FIG. 8 are illustrations of UV-C devices constructed in accordance with the principles of the present invention.

Device 850 may be, for example, a different perspective of device 840 of FIG. 8. Chamber 856 may be utilized, for example, to provide fans for providing air through device 850. Mounting surface 851 and 854 and mounting apertures 852 and 855 may be provided. Curved surface trough 853 may be provided to provide a flat surface for interfaces. Persons skilled in the art will appreciate that manual interfaces and visual indicators (e.g., displays) may be provided on curved surfaces (e.g., a flexible display on a curved portion of a device).

Device 860 may be a perspective looking at an end of a device such as an end of device 840 of FIG. 8. Fan channel 862 may be provided and housing 861 may be provided.

Device 870 may be provided and may include housing 871. Device 880 may be, for example, a perspective of cross section 872 of device 870 of FIG. 8. Device 880 may include fan structure 881, which may include a pair of counterrotating compression fans, and fan structure 992, which may include a pair of counter-rotating compression fans. Outlet 883 may push air, for example, to an inactivation working area (e.g., an inactivation working area provided by a UV-C reflective tube.

Device 890 may be, for example, a different perspective of device 880 that may include, for example, fan structure 892 which may be mounted above a different fan structure each of which may include one or more fans such as two counter-rotating fans. Structure 891 may be provided to mount objects to such as, for example, airflow fans. Persons skilled in the art will appreciate that fans may be provided in a device and may provide airflow at rates above 400 liters per minute (e.g., above 500 liters per minute). Multiple circuit boards with UV-C arrays may be placed around multiple tubes. Tubes of any width and fans of any width may be provided. For example, four flexible circuit boards may be provided about one or more in-line tubes that may have inner diameters between twenty-five and fifty millimeters (e.g., between 30 and 33 millimeters0 and air may be driven through the working area to inactivate pathogens at speeds of at least 1,000 liters per minute, at least 1,500 liters per minute, or at least 2,000 liters per minute.

A substance inactivation device may include heat sink fins (e.g., aluminum fins) coupled to heat sinks (e.g., copper and/or aluminum heat sinks such as an aluminum heat sink with copper heat transportation structures such as rods within the aluminum). Heat sinks may be a heat sink structure that couples to, for example, a flexible circuit board coupled to tube 825. Tube 825 may have a different shape on its external surface (e.g., a six sided shape) than the shape on its internal surface (e.g., a spherical cylinder). A tube for defining a working area may be fabricated, for example from a UV-C reflective material (e.g., PTFE) and may have apertures for placing UV-C transparent materials (e.g., quartz) so UV-C light from UV-C LEDs on a flexible circuit board placed on the exterior of the tube may flow through the UV-C transparent materials and enter a working area provided by the tube. Person skilled in the art will appreciate that the number of sides on the external surface of a tube providing a working area) may match the number of UV-C LED locations that are provided about the perimeter of that tube. For example, if there are six possible UV-C LED locations about an external surface perimeter of a tube providing a working area then that tube may have six sides on the external surface. Persons skilled in the art will appreciate that the external surface of the tube may be any shape (e.g., spherical) and may match the shape of the internal surface of that tube. A tube may be fabricated from multiple materials such as, for example, a tube of UV-C transparent material (e.g., quartz) that is coated (e.g., either on its interior or external surface) with a UV-C reflective material (e.g., aluminum) with spaces in the UV-C reflective material aligning with UV-C locations. Structures may be provided and may be utilized to provide a mechanical support structure for attaching pieces. A structure may also be, for example, a heat sink. A portion that generates or conducts heat may be provided with or without heat sink fins. Additional heat sink or heat sinks may be provided and may attach to such a portion. A heat sink may thermally couple to one or more sides of a flexible circuit board, or other structure as a non-flexible circuit board, that provides UV light sources (e.g., UV-C LEDs). For example, a heat sink may be thermally coupled to UV sources located on two sides of the exterior of a tube providing a working area. Any number of screw and/or mounting holes and/or structures may be provided on any structure of a substance sanitization device such as an air or liquid sanitization device. Persons skilled in the art will appreciate that different wavelengths of light (e.g., different wavelengths of UV-C, UV-B, and/or UV-C, and/or sub 100 nm and or wavelengths greater than UV-A) may be provided about a tube providing a working area to insert light of that wavelength into working area. Different wavelengths of light may, for example, provide improved different treatments for different types of contaminants. For example, one type of UV treatment may be utilized to optimize inactivation of virus using a photonic effect targeting the uracil of a virus while another type of UV treatment may be utilized to optimize impact of contaminants using a photonic effect targeting the thymine of a contaminant. Heat conductive materials such as heat sinks and heat sink fins may be attached to structures and each other using, for example, heat transfer pads (e.g., thermal pads) and/or heat transfer substances (e.g., thermal paste).

A device may be provided that may include fan blade operated by a motor that provides a working substance through the inlet of a working area so the substance can receive one or more types of treatments (e.g., a heat treatment and a UV-C treatment). Persons skilled in the art will appreciate that multiple types of treatments may be utilized.

For example, heat may be introduced into a working area (e.g., by active heat generators or by heat sinks providing heat into a working channel) in order to impact a contaminant (e.g. inactivate a contaminant or render a contaminant inoperable). A tube may be provided to provide a treatment working area. A working area may be fabricated from one part or from multiple parts mechanically removably attached or permanently fixed (e.g., welded and/or adhered) together. An output may be provided so that air may flow out of a treatment working area. Persons skilled in the art will appreciate that materials forming an inlet and/or outlet may fabricated from different materials from a portion of a working area structure between an inlet and outlet. For example, the inlet and outlet portions may be non UV-C reflective on their surfaces facing a treatment working area such that UV-C does not reflect off those surfaces and out of the treatment working area. Furthermore, for example, any number of inlets and or outlets may be provided into a working area. For example, a working area may have one inlet and two or three or more outlets. As per another example, a working area may have one outlet and two or three or more inlets. As per another example, a working area may have two or three or more inlets and outlets and the number of inlets and outlets may be the same or may be different. Inlets and/or outlets may have different sizes and shapes and interior and exterior surface shapes and may be fabricated as one part or multiple parts form one or more of the same or different materials using one or more of the same or different processes. A substance may flow out through an output and may, for example exit a device and enter the environment of the device (e.g., in a ventilator setting may exit a UV-C sanitization device and enter a ventilator tube) or may enter a room (e.g., an elevator, hotel room, cruise ship room) with sanitized air. As per another example, treated air may be flow out of an outlet through a channel and may leave the device or chamber through one or more apertures in structure providing that channel. After treated air leaves a portion of the device, the air may exit the device or may be flowed into another chamber. Persons skilled in the art will appreciate that UV-C LEDs may be mounted to the exterior of a tube providing a working area as well as one or more heat sinks and air may be flowed across the exterior of the tube providing the working channel (e.g., over surfaces of the heat sinks across the tube providing the working channel) and out through an outlet channel. In doing so, for example, treated air may be utilized to also remove heat from the device. In doing so, for example, air is not circulated from device 830 that is not treated. In circulating untreated air, a device may introduce more contaminants into a portion of an environment by more quickly spreading contaminated air. Additionally, certain contaminants may be impacted by heat. Accordingly, the removal of heat may provide, for example, a second type of treatment in order to increase the inactivation of contaminants and/or render more contaminants inoperable.

Persons skilled in the art will appreciate that an access door may be provided on one or more areas of an UV-C generating device and may be, for example, aligned with an outlet or an aperture of a tube providing a working area so that the access door may be opened and a cleaning brush may be utilized to clean the interior of the working channel. A lock may be provided on the access door and a keyhole may be provided on the lock so a key may be utilized to open the lock. Other security mechanisms can be provided such as, for example, a keypad entry that utilizes an entry code or a biometric access lock (e.g., fingerprint and/or retinal). Persons skilled in the art will appreciate that a UV-C generating device may be able to detect the status of an access door (e.g., whether the access door is opened or closed) and the device may restrict the UV-C light sources from turning on until circuitry confirms the access door is closed. Any number of access doors may be provided such as, for example, an access door about an inlet to receive a particulate filter which could also, for example, be utilized to receive a cleaning utensil (e.g., brush) and the cleaning utensil may be able to attach to and be removed from a structure located on the device. A chain or rope or other flexible structure may be utilized to keep the cleaning utensil secured to device 830 even when the cleaning utensil is removed from an attachment structure to the device and is being utilized by a user. Additionally, for example, a movable (e.g., pivotable) air direction fin (or fins) may be provided at inlet 834 so that, for example, air may be pointed to different areas of a working area. Doing so may, for example, increasing the impact of a cleaning protocol such that a cleaning protocol that increases airflow into a working are to clean the working area may be moved to provide air at different locations in order to improve the impact of the cleaning process.

A UV-C inactivation device may include any number of UV-C generating devices (e.g., three, four, more than four). Each UV-C generating device may be utilized, for example, to sterilize air and may include one or more fans (e.g. two fans each with two counter-rotating blades) to bring air into a working channel of the UV-C generating devices. A structure may be utilized to fix the UV-C generating devices together and may be utilized for example in a passageway such as an air duct.

Figure 9:
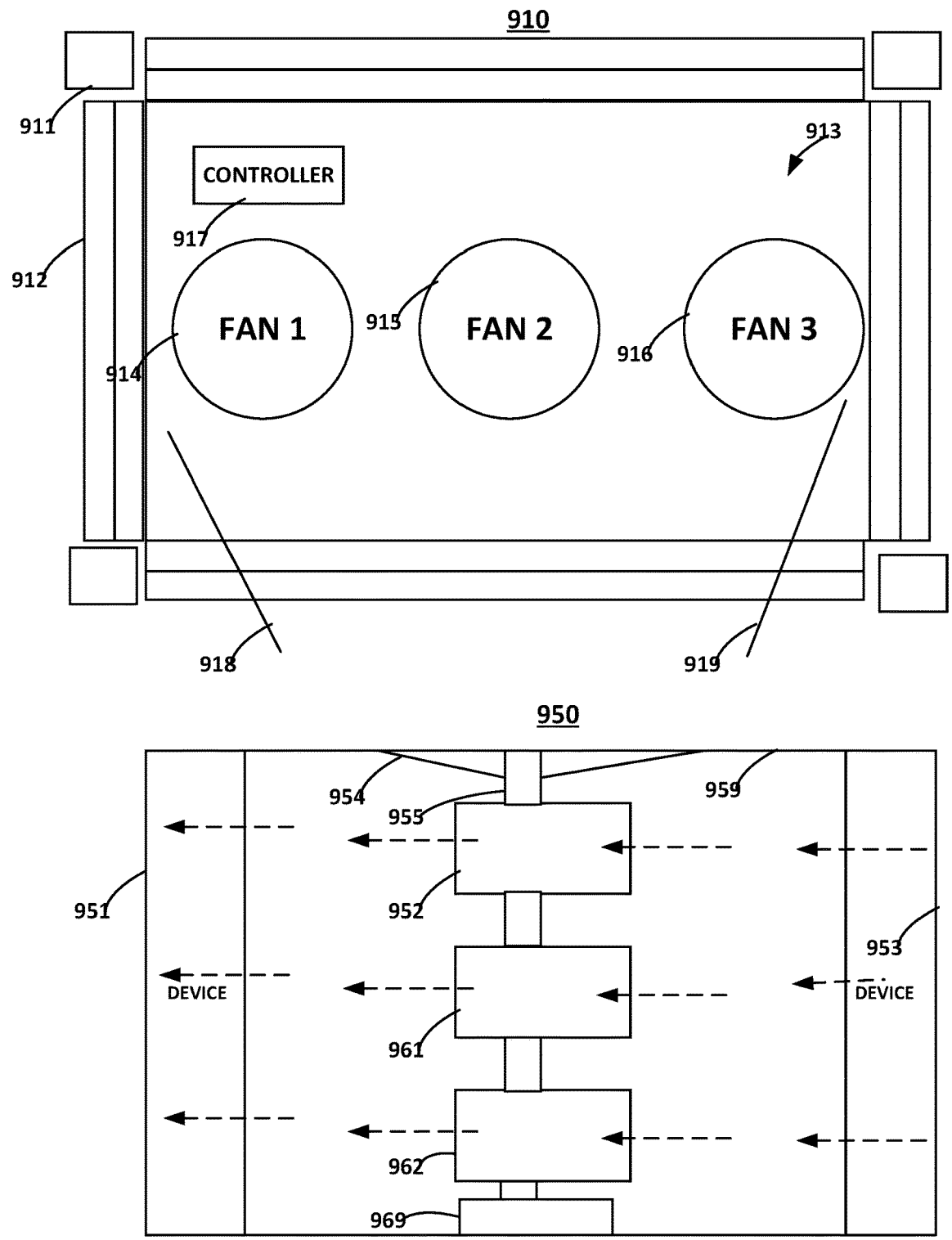
FIG. 9 are illustrations of UV-C devices constructed in accordance with the principles of the present invention.

FIG. 9 shows device 910 for air sanitization in an air passage such an air duct that may include air blockage structure 913, UV-C air sanitization fan 914, UV-C air sanitization fan 915, UV-C air sanitization fan 916, controller 917, brace 918, brace 919, expandable air blockage structure 912 and removable and insertable air blockage structure 911. Persons skilled in the art will appreciate that a scalable air sanitization device may be placed in multiple size air ducts and may be placed, for example, after an air register (e.g., a 200 CFM to 500 CFM air register). Controller 917 may control, for example, the intensity of UV-C light in each fan as well as the speed of air being introduced each fan to maintain a particular level efficacy. Controller 917 may determine, for example, humidity and may make adjustments based on humidity and may share data with, and be controlled by or share controls with, a remote system (e.g., remote HVAC control system). Persons skilled in the art will appreciate that a fan of a UV-C air sanitization device may not be utilized (e.g., not be included) and the air flow created by an air flow system to the air duct may be utilized to organically transfer air through working areas of UV-C generating devices. UV-C inactivation devices 914, 915, and 916 may be, for example devices 440 of FIG. 4. The aerosolization inactivation devices may be, for example, aligned horizontally, staggered, or put in any location (e.g., four inactivation devices may be put about each corner of structure 910).

System 950 may include one or more UV-C air sterilization devices for sterilizing air flowing from device 953 to device 951. UV-C air sterilization devices may be included as part of air blockage structure 955 and one or more braces 954 to brace against air duct 959. Stand 969 may be included to provide additional support for device 952 and structure 955. Person skilled in the art will appreciate that device 953 and 951 may be, for example, air flow registers.

Inactivation device 952, 961, and 962 may be, for example, device 420 of FIG. 4.

Persons skilled in the art will appreciate that any types of fans may be provided on an air or virus or liquid inactivation device such as centrifugal and/or axial fans.

Figure 10:
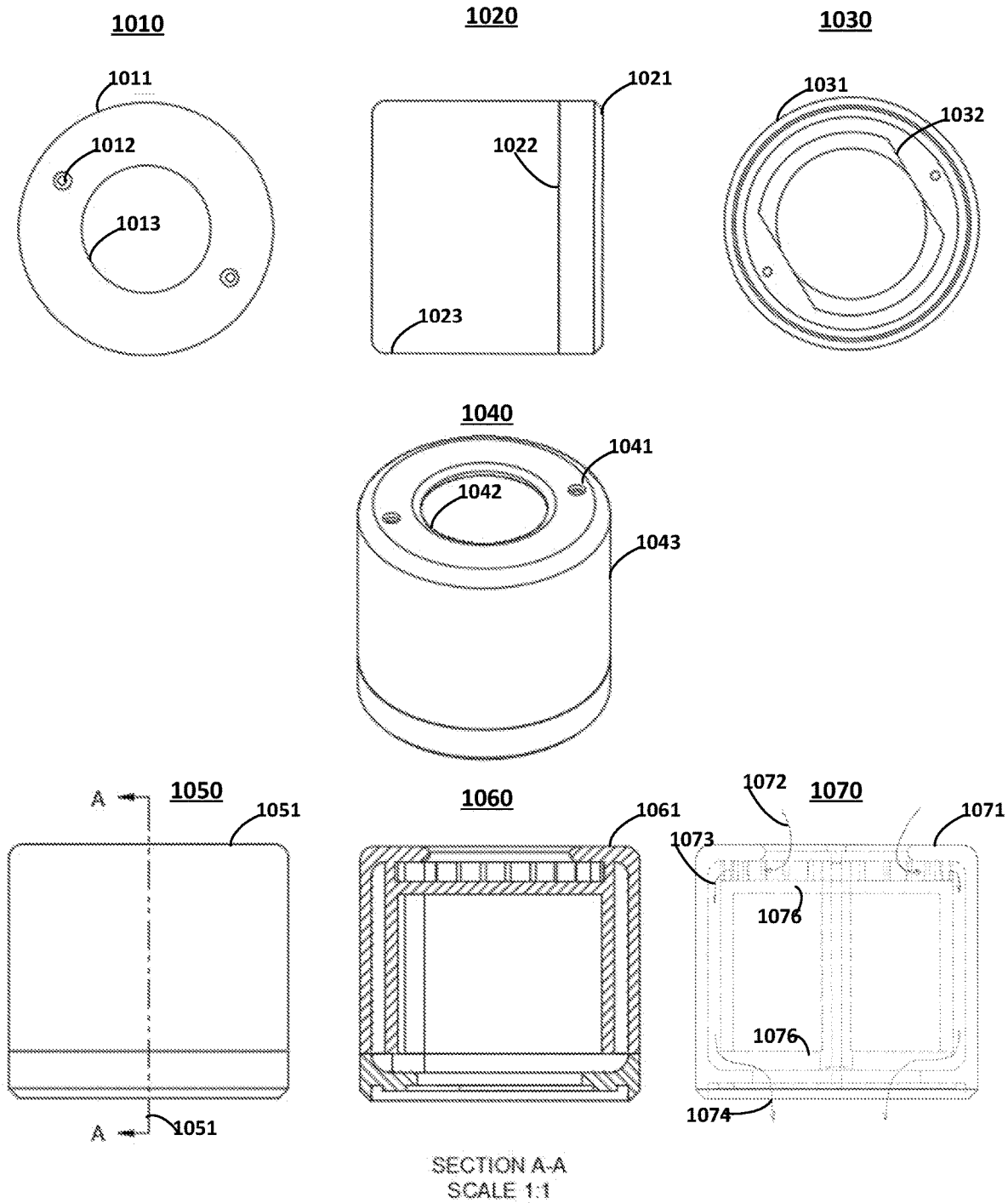
FIG. 10 are illustrations of UV-C devices constructed in accordance with the principles of the present invention.

FIG. 10 shows structure 1010 which may include housing 1010, airflow channel aperture 1013, and one or more screws (e.g., screw 1012). Structure 1020 may be, for example, a different perspective of structure 1010. Structure 1010 may be a sound suppression structure to suppress sound generated by sound generating structures of a device (e.g., sound generating motors and fans of a device). Structure 1020 may be a single structure or may be multiple structures fixed together (e.g., structure 1022 and 1023). Angled edge 1021 may be provided and may include an airflow aperture.

Device 1030 may be a perspective of a device with an air suppression structure that may include aperture 1030. Aperture 1030 may be utilized to affix multiple types of panels such as, for example, a panel with a grate so that air may flow through the grate but materials larger than the apertures of the grate are stopped by the grate. Alternatively, aperture 1030 may be utilized to receive a panel with a smaller aperture for receiving air than aperture 1030. Structure 1030 may include housing structure 1031.

FIG. 10 shows structure 1040 which may be a sound suppression structure and may include housing structure 1043. Attachment structures such as structures 1041 may be utilized to attach panels (e.g., panel 1042) to a structure (e.g., structure 1043) of structure 1040.

FIG. 10 shows structure 1050 that may provide sound suppression from sound generated in a UV-C aerosolization inactivation device. Structure 1060 may be a cross-sectional view of structure 1050 across cross section 1051. Structure 1070 shows airflow of a structure, such as structure 1060, where air flows through structure 1071 through path 1071 and through path 1073 and exists structure 1070 from path 1074. Structure 1075 may be utilized to suppress sound being generate by fans and motors of coming from the side of path 1074 and emanating to the side of structure 1071. Sound suppression material (e.g., soundproofing such as soundproofing foam) may be placed in the chamber between structures 1075 and 1076.

Persons skilled in the art will appreciate that UV-C LEDs may, for example be between 250 and 290 nm or, more particularly, between 260 and 280 nm or, more particularly, between 260 and 270 nm, or more particularly, between 260 and 265 nm, or more particularly be approximately 262 nm. Person skilled in the art will appreciate that each UV-C LED may, for example, provide UV-C light at an energy of at least 20 milliwatts or more or, more particularly, at an energy of at least 50 milliwatts or more or, more particularly, at an energy of at least 70 milliwatts or more.

Persons skilled in the art will appreciate that UV-C air sanitation devices may be used for any UV-C sterilization purpose such as UV-C inactivation of viruses to create vaccines, and/or sanitize liquids, etc).

Figure 11:
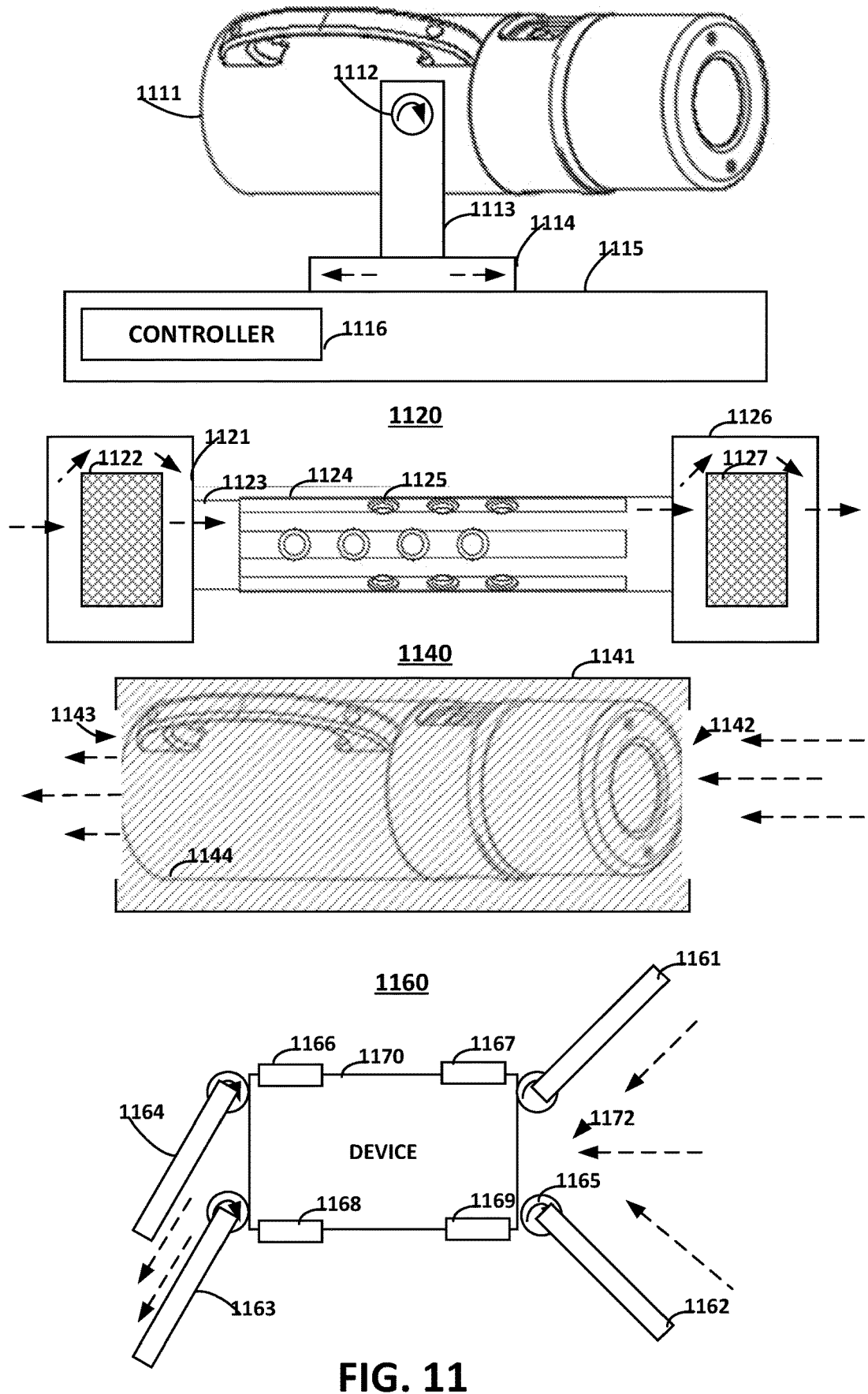
FIG. 11 are illustrations of UV-C devices constructed in accordance with the principles of the present invention.

FIG. 11 shows device 1110 that may include a multiple axis oscillator for moving a UV-C generating device (e.g., a UV-C air inactivation device) to move UV-C inactivation device 1111 to increase the scope of airflow intake and increase the scope of airflow outtake of device 1111. Device 1111 may be, for example, rotated about axis 1112 in any direction and at any speed and at any acceleration or combinations thereof. Controller 1116 may provide control signals to motors controlling the position and movement of device 1111. Persons skilled in the art will appreciate that controller 1116 may be located in device 1111 (e.g., as program logic on a processor located in device 1111). Structure 1113 may be structured about motorized structure 1114 which also may be moved in any direction, at any speed, and at any acceleration, or combination thereof. Persons skilled in the art will appreciate that device 1111 may be moved about one, two, or more than two axis.

FIG. 11 shows structure 1120, which may be a working channel chamber for inserting UV-C light through apertures 1125 across tube 1124. Tube 1124 may ha an inner surface of UV-C reflective material (e.g., PTFE). Mating structure 1123 may be UV-C reflective material (e.g., on its interior surface) so that UV-C light introduced into tube 1124 may be reflected inside the tube and utilized to inactivate contaminants (e.g., virus). Structure 1121 may be UV-C reflective material and may include UV-C material 1121. U-VC material may reflect UV-C light that leaves tube 1124 to reflect UV-C light back into tube 124. Structure 1126, which may be UV-C reflective, and UV-C structure 1127, which may be UV-C reflective may be utilized to reflect UV-C light leaving tube 1124 back into tube 1124 while permitting airflow to occur around material 1127.

FIG. 11 shows device 1140 which may include UV-C air contaminant inactivation device 1144 and may include sound suppression peripheral 1141 that may be placed around device 1144 to suppress sound from leaving sound suppression peripheral 1141. Apertures may be provided in structure peripheral 1141 and may permit air to flow through aperture 1142 and out of aperture 1143. Peripheral 1141 may be sold separately than device 1144 and may be removably fixed to device 1144.

FIG. 11 includes housing 1160 that may include device 1170 that may be utilized, for example, to inactivate objects in substances brought through housing 1170. Such a substance may be, for example, a gas (e.g., air), liquid (e.g., blood), or any type of substance. An inactivation device may include movable intake fins 1161 and 1162 (e.g., rotated about axis 1165) and movable outlet fins 1164 and 1163 movable by, for example, motors. Adjustable air ports 1166-1169 may be included and may be opened and closed (e.g., and moveable fins may be provided or may moveable ports 1166-1169 themselves). Ports 1166-1169 may be opened or closed fully or partially to permit additional air inlets and/or outlets to provide different intake patters and outtake patterns. In managing the direction and locations of air inflow and outflow device 1160 may be configured different for different environments to provide different intake and outtake air pathways.

Figure 12:
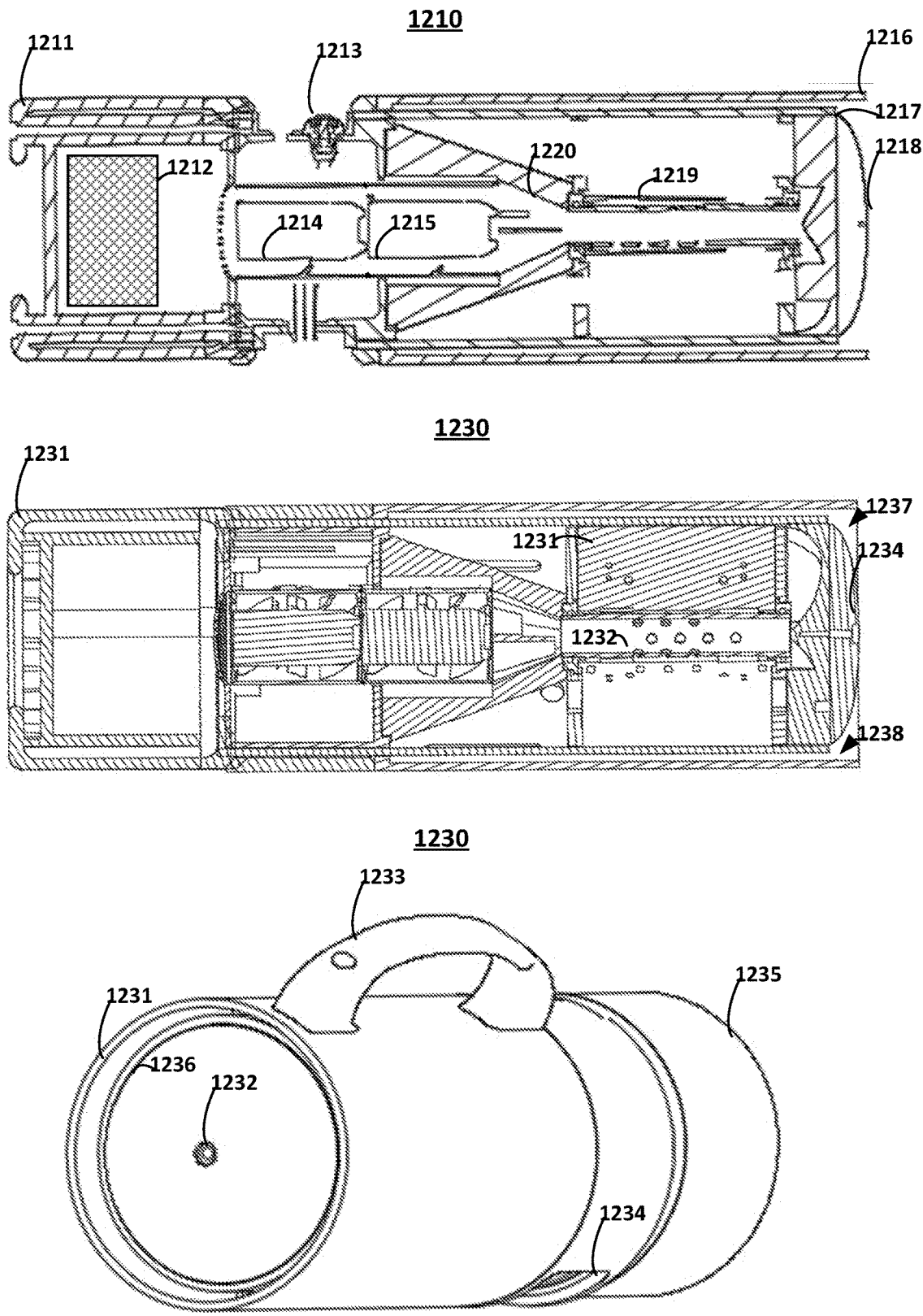
FIG. 12 are illustrations of UV-C devices constructed in accordance with the principles of the present invention.

FIG. 12 shows device 1210, which may be utilized to provide UV-C into a working area. Sound suppression structure 1211 may be provided and may include soundproofing 1121. Manual interface 1213 may be provided and may include control signals to control fans structures 1214 and 1215 (e.g., which may each be a pair of counter-rotating fans such as compression fans). Funnel 1220 may be provided to funnel air through tube 1219 which may be surrounded by one or more UV light sources (e.g., UV-C light sources or a variety of different types of UV-C, UV-A, and/or UV-B light sources and/or non-UV light sources) to provide light into a structure that may reflect the light provided into the structure. Heat sinks may remove heat and inactivated air may flow past any heat sinks and any heat sink fins and may be ejected from device 1210 between, for example, edge 1216 and 1217. Dome 1218 may be provided which may influence the movement of air being pushed out of deice 1210. Mechanical structures may be provided to spiral air pushed out of the device for applications where, for example, spiraled air may be desired.

FIG. 12 shows structure 1230 that may include housing 1231, dome 1234, tube 1232, and heat sink 1231. Air may be provided through tube 1232, past heat sink 1231, and through channels 1237 and 1238.

FIG. 12 shows device 1230 which include structure 1235, which may be a sound suppression structure, manual interface aperture 1234 may be provided which may have manual interfaces as well as visual indicators such as one or more displays, handle 1233, domed outlet area 132 and outlet channel between edge 1231 and 1236.

Persons skilled in the art will appreciate that UV-C transparent materials may have at least 80 percent, 90 percent, 92 percent, or more than 92 percent UV-C transparency. UV-C LEDs may provide, for example, light between 220 and 280 nanometers (e.g., between 255 and 275 nanometers). A device may have, for example, at least 10, at least 20, and at least 30 UV-C LEDs.

Persons skilled in the art will appreciate that a UV-C LED may produce visible spectrum light and that one or more visible light sensors may be utilized to detect this light in order to, for example, detect the amount of UV-C in a working area to determine, for example, if a cleaning process should be initiated. Each UV-C LED may be operated independently and the amount of visible spectrum light compared to stored information associated with a clean state (e.g., a state when the device was manufactured or initially tested). In doing so, for example, the cleanliness of UV-C transparent material for a particular UV-C LED may be determined. Accordingly, a tube that provides a working area may have recessed portions and apertures associated to visible light sensors (and/or other sensor) and such sensors may be located at, for example, about each inlet/outlet of a device. Such sensors may be tilted to face into a working channel such that more light is received. In addition, or instead of, testing each light source independently (e.g., each UV-C light source independently) the UV-C LEDs may be tested in groups and may be tested multiple times. All the UV-C LEDs may also be turned on and light sensed to determine a cleanliness profile for the device. In sensing multiple different UV-C LEDs operating at different times, a cleanliness profile may be determined for each UV-C transparent material that is associated with each LED as well as the cleanliness of different areas of UV-C reflective materials (or other materials) that may be provided on an inner surface of a working area. Persons skilled in the art will appreciate that visual indicators (e.g., light sources and/or displays) may be utilized to provide feedback on cleanliness and the cleanliness of different portions of a device as well as estimated sterilization impact at different operating modes. Furthermore, manual inputs may be provided so a user can perform a cleaning profile diagnostic so that after a cleaning a user can confirm the level of cleanliness that exist sin the device. Persons skilled in the art will appreciate that a cleanliness profile diagnostic may also, for example, be utilized to indicate if a UV light source is estimated to not be operational or operational at a particular diminished capacity. The operation of a device may be changed (e.g., autonomously) based on sensed data such as, for example, additional UV light sources may be activated and/or the intensity of particular UV-C sources may be increased.

Persons skilled in the art will appreciate that a light source calibration process may be utilized to calibrate devices. Efficacy levels may be adjusted based, in part, on calibration data. Integrating sphere(s) may be utilized as part of a process to calibrate UV-C LEDs based on determined output and controlled thresholds. Persons skilled in the art will appreciate that fiber optics may be utilized to transport UV light, such as UV-C light, to a working area, such as a tube. Multiple UV-C LEDs may be optically connected to UV-C fiber optics and these fiber optics may be combined through a UV-C fiber optic combiner and the combined UV-C fiber optic may be provided through, for example, an aperture of a structure (e.g., a tube) having a working area for receiving UV-C. UV-C optical modifiers may be provided at the end of a combined UV-C fiber optic to provide different UV-C output profiles.

Persons skilled in the art will appreciate that elements of any device herein may be utilized in any device herein. Persons skilled in the art will also appreciate that the present invention is not limited to only the embodiments described. Instead, the present invention more generally involves UV-C focus, amplification, and control. Persons skilled in the art will also appreciate that the apparatus of the present invention may be implemented in other ways then those described herein. All such modifications are within the scope of the present invention, which is limited only by the claims that follow.

What is claimed is:

1. A device comprising:
   a housing having a fan for bringing an external air into said housing;
   a sound suppression chamber for suppressing sound created by said fan; and
   a plurality of ultraviolet type-C light emitting diodes, at least a portion of which are located on one or more flexible printed circuit boards that are located around a working area that receives said external air, wherein at least two of said plurality of ultraviolet type-C light emitting diodes are centered at a wavelength between 250 and 275 nanometers, wherein at least a portion of said plurality of ultraviolet type-C light emitting diodes are capable of being independently controlled, wherein said flexible printed circuit boards enable adjustment of position and orientation of said ultraviolet type-C light emitting diodes within said housing enabling customizable targeting of ultraviolet type-C light within said working area, and said ultraviolet type-C light emitting diodes are operable to provide ultraviolet light to said working area.

2. The device of claim 1, wherein said sound suppression chamber is provided in said housing.

3. The device of claim 1, wherein said external air travels through said fan, said sound suppression chamber receives said external air before said external air is received by said fan.

4. The device of claim 1, wherein said sound suppression chamber include a sound suppression material.

5. The device of claim 1, wherein said sound suppression chamber includes a sound suppression material at least two inches thick at a thickness point and at least two inches wide at a width point and at least two inches long at a length point.

6. A device comprising:
   a housing having a fan for bringing an external air into said housing;
   a human perceivable notification system; and
   a plurality of ultraviolet type-C light emitting diodes, at least a portion of which are located on one or more flexible printed circuit boards that are located around a working area that receives said external air, wherein at least two of said plurality of ultraviolet type-C light emitting diodes are centered at a wavelength between 250 and 275 nanometers, said ultraviolet type-C light emitting diodes are operable to provide ultraviolet light to said working area, and wherein at least a portion of said plurality of ultraviolet type-C light emitting diodes are capable of being independently controlled, wherein said flexible printed circuit boards enable adjustment of position and orientation of said ultraviolet type-C light emitting diodes within said housing enabling customizable targeting of ultraviolet type-C light within said working area, and wherein said human perceivable notification system is operable to provide a plurality of human-perceivable notifications of different non-zero percent ranges of inactivation of a virus for said external air that travels through said working area.

7. The device of claim 6, wherein said human perceivable notification system includes a light emitting diode in the visible spectrum that does not provide UV-C light.

8. The device of claim 6, wherein said human perceivable notification system includes a plurality of light emitting diode in the visible spectrum that does not provide light to said working area.

9. The device of claim 6, wherein said human perceivable notification system includes a display.

10. The device of claim 6, wherein said human perceivable notification system includes a speaker.

11. The device of claim 6, wherein a fiber optic is optically coupled to at least one of said plurality of said ultraviolet type C light emitting diodes.

* * * * *